United States Patent [19]

Takamizawa

[11] Patent Number: 5,134,547
[45] Date of Patent: Jul. 28, 1992

[54] ELECTRIC APPARATUS HOUSING AN ELECTROMAGNETIC WAVE NOISE GENERATING SOURCE

[75] Inventor: Kazufumi Takamizawa, Tokyo, Japan
[73] Assignee: Olympus Optical Co., Ltd., Tokyo, Japan
[21] Appl. No.: 473,243
[22] Filed: Jan. 31, 1990

[30] Foreign Application Priority Data

Feb. 11, 1989 [JP] Japan .................................. 1-287109
Apr. 13, 1989 [JP] Japan .................................. 1-96098
Dec. 20, 1989 [JP] Japan .................................. 1-332264

[51] Int. Cl.⁵ .............................................. H05K 9/00
[52] U.S. Cl. ...................................... 361/424; 358/98; 174/35 R
[58] Field of Search ................... 174/35 R, 35 MS; 361/380, 424; 128/4, 6; 358/98; 219/10.55 R, 10.55 D

[56] References Cited

U.S. PATENT DOCUMENTS

| | | | |
|---|---|---|---|
| 3,493,760 | 2/1970 | Hoadley | 250/199 |
| 4,232,359 | 11/1980 | Leon et al. | |
| 4,291,961 | 9/1981 | Takayama | 354/62 |
| 4,711,979 | 12/1987 | Glasser et al. | 219/10.55 D |
| 4,831,211 | 5/1989 | McPherson et al. | 174/35 R |

FOREIGN PATENT DOCUMENTS 0381273 8/1990 European Pat. Off. .......... 174/35 R
60-262369 12/1985 Japan .
62-23499 2/1987 Japan .

Primary Examiner—Leo P. Picard
Assistant Examiner—Bot L. Ledynh
Attorney, Agent, or Firm—Armstrong & Kubovcik

[57] ABSTRACT

An electric apparatus reducing the radiation of electromagnetic wave noise according to this invention includes an inner case in which an electromagnetic wave generating source is housed an a first opening for replacing the electromagnetic wave generating source is formed. An inner door is kept conductive with the inner case and closes the first opening to enclose the electromagnetic wave generating source together with the inner case. A case houses the inner case and has a second opening for replacing the electromagnetic wave generating source and an opening and closing door for closing the second opening.

21 Claims, 24 Drawing Sheets

FIG.23
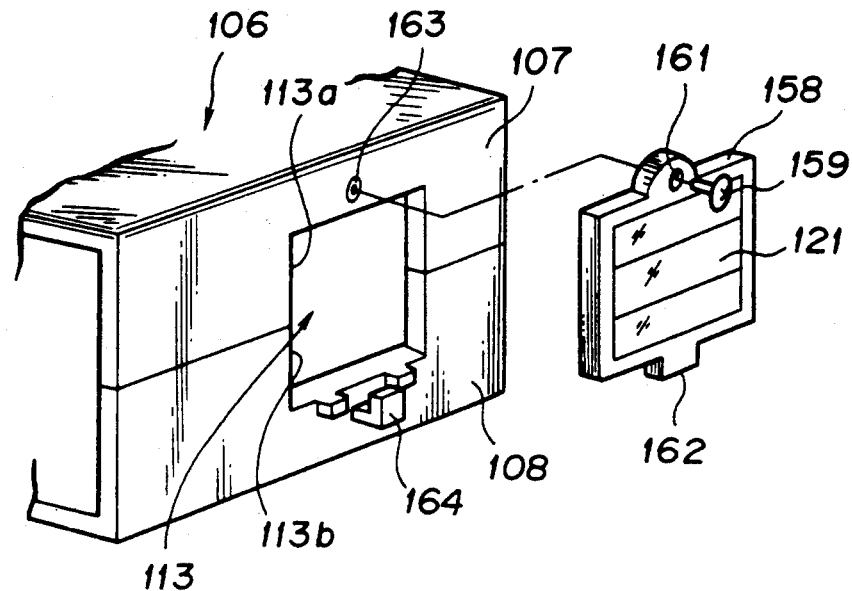
FIG.24 (a) FIG.24 (b) FIG.24 (c)
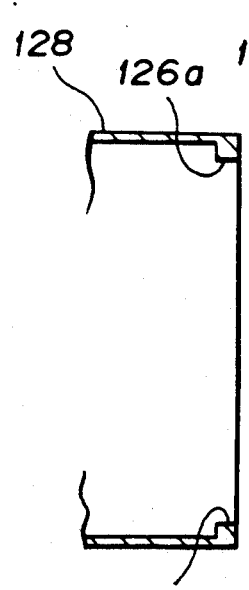
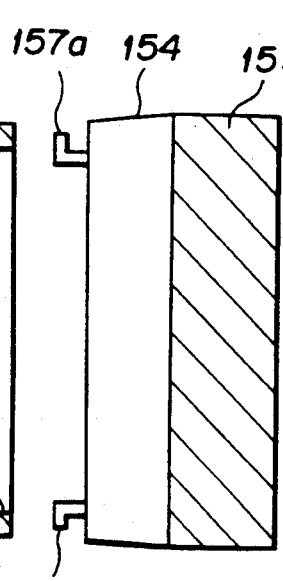
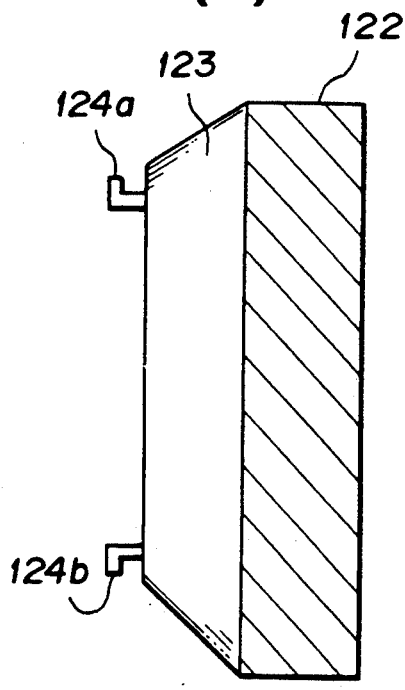

FIG. 29
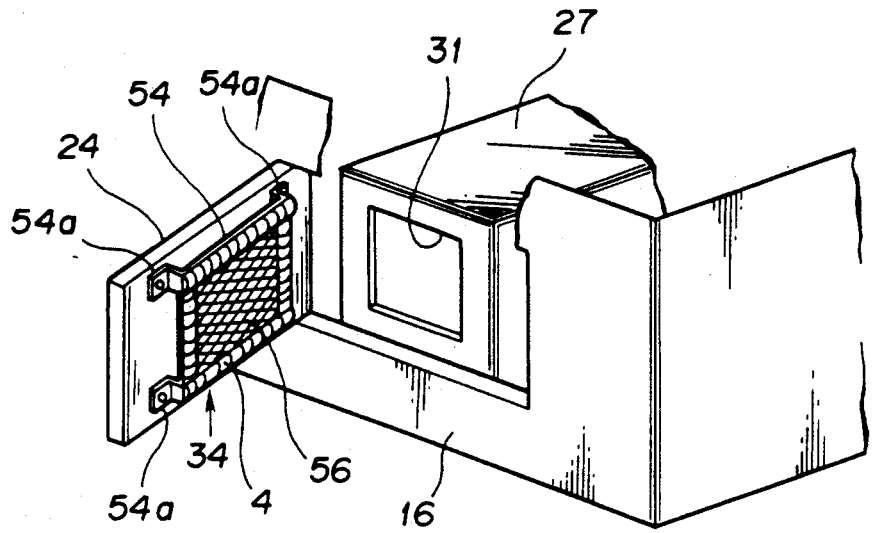
FIG. 30
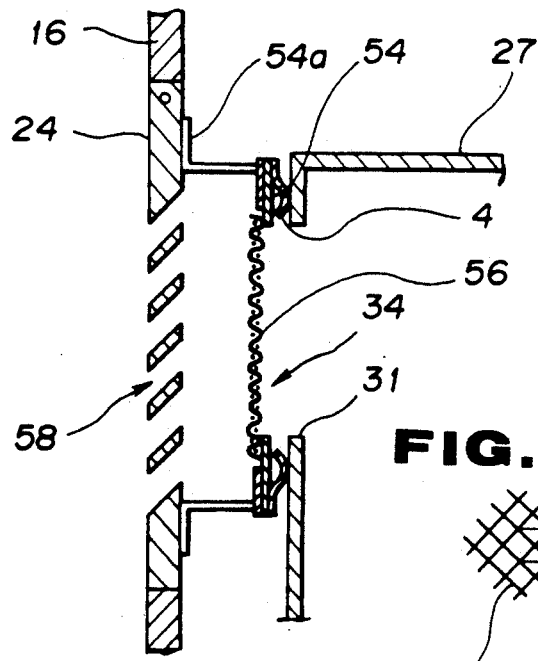
FIG. 31(a) FIG. 31(b)
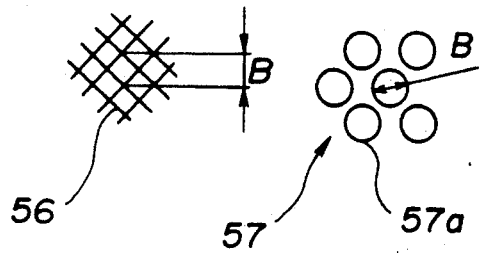

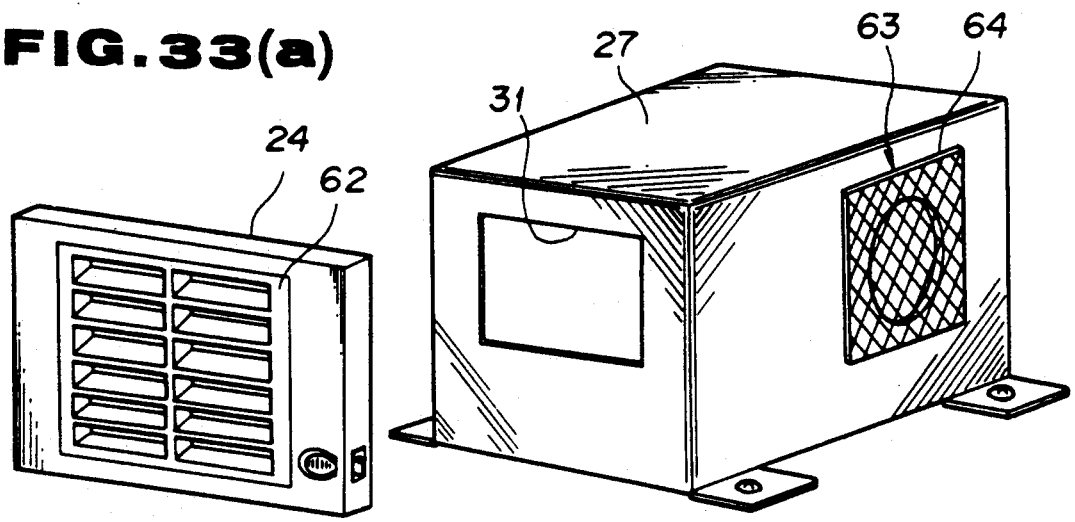
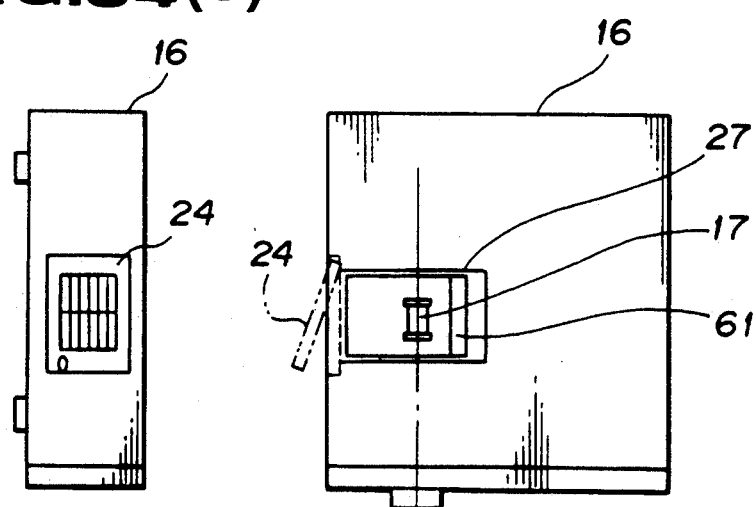
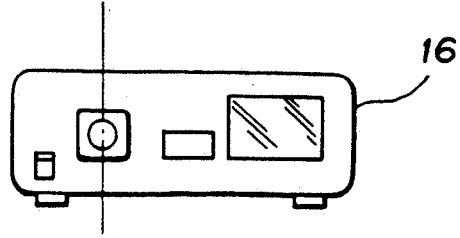

5,134,547

ELECTRIC APPARATUS HOUSING AN ELECTROMAGNETIC WAVE NOISE GENERATING SOURCE

FIELD AND BACKGROUND OF THE INVENTION

This invention relates to an electric apparatus having an opening formed to replace an electromagnetic wave noise generating source.

Recently, the development of the electric device field is so remarkable that the signal components and frequency components handled therein are many and various. Also, from another point of view, in order to reduce the weight and cost of the devices, the materials of the cases are changing from metals to plastic or the like. Under such circumstances, the obstacle by electromagnetic waves discharged from electric devices has become such a great problem that countermeasures against electromagnetic waves have been applied to electric devices. For example, a case made of plastic is painted on the inside with a shielding electroconductive paint so as to be conductive. Also, as in FIGS. 1 to 3, in the gap of an opening and closing door 2 provided in a case 1 or the jointing part between the case 1 and a front panel 3, such an electroconductive finger member 4 as is generally used for a shielding room opening and closing part and is shown in FIGS. 3(a)-3(b) is provided to intercept electromagnetic wave noise with the case outer fitting. The electromagnetic finger member 4 shall be explained in the following. The electroconductive finger member 4 shown in FIGS. 3(a)-3(b) has a band-like fitting part 4a and a plurality of finger parts 4b extending from the edge of this fitting part 4a and curved to be U-shaped as in FIG. 3(b).

The above mentioned fitting part 4a is fitted to the front panel 3 shown, for example, in FIGS. 3(a)-3(b) so that, when the front panel is fitted to the case 1, the finger parts 4b will be pressed against the case and will be elastically transformed so that the case 1 and front panel 3 may be positively electrically conductive.

FIG. 1 is a perspective view of an electric device.
FIG. 2 is a sectioned view on line A—A' in FIG. 1.
FIG. 3(a) is a plan view of an electroconductive finger member 4. FIG. 3(b) is a sectioned view on line B—B' in FIG. 3(a).

However, in the prior art shown in FIGS. 1 to 3(a)-3(b), the electromagnetic wave shielding effect is not sufficient and the appearance is ugly.

Also, in case an electromagnetic wave noise generating source and various circuits are provided within an electric apparatus, it will be necessary to shield the electromagnetic wave noise generating source on the periphery in order to reduce the influence of the electromagnetic wave noise on the circuit from the electromagnetic wave noise generating source but, in case the electromagnetic wave noise generating source is a lamp provided within a light source apparatus feeding an illuminating light, for example, to an endoscope, it will be necessary to replace the lamp due to a breakdown or the like and therefore an opening for the replacement will be provided in a shielding box. As a result, there has been a problem that the shielding can not be perfectly made.

In the publication of Japanese Utility Model Application Laid Open No. 23499/1987 is shown an art comprising a shielding case having an opening formed on one side surface, an electric part contained in this shielding case, a lid closing the opening of the shielding case, a recess through which are passed lead wires connected to the electric part formed in the opening of the shielding case and a shielding piece provided in this recess as substantially parallelly separated from and opposed to the inner surface of the lid. However, even in this prior art, the electromagnetic wave noise can not be well intercepted.

OBJECT AND SUMMARY OF THE INVENTION

An object of the present invention is to provide an electric apparatus which is a case housing an electromagnetic wave noise generating source, which reduces the radiation of electromagnetic wave noise out of the case from the electromagnetic noise generating source and the influence of the electromagnetic noise on the circuit provided within the case and which is favorable in appearance.

The electric apparatus of the present invention comprises a case having an electromagnetic noise generating source built-in, an inner case housing the electromagnetic noise generating source within the case and having an opening for replacing the electromagnetic wave noise generating source formed and an inner door conductive with the inner case and enclosing the electromagnetic wave noise generating source together with the inner case in case the closable opening is closed.

In the electric apparatus formed as mentioned above the electromagnetic wave noise generating source is housed within the inner casing replaceably through the opening. The opening is closed with the inner door. In the case of closing the opening, the inner door will be conductive with the inner case and will enclose the electromagnetic wave noise generating source together with the inner door.

BRIEF DESCRIPTION OF THE DRAWINGS

FIGS. 1 to 3(a)-3(b) relate to a prior art.
FIG. 1 is a perspective view of an electric device.
FIG. 2 is a sectioned view on line A—A' in FIG. 1.
FIG. 3(a) and (b) are explanatory views of an electroconductive finger member.
FIGS. 4 to 24 relate to the first embodiment of the present invention.
FIG. 4 is an appearance view of an endoscope apparatus.
FIG. 5 is an explanatory view of an opening and closing part.
FIG. 6 is a perspective view of the opening and closing part.
FIG. 7 is a schematic formation view of a light source apparatus.
FIG. 8 is a circuit diagram of the light source apparatus.
FIG. 9 is a perspective view for explaining the disassembly of a lamp house.
FIG. 10 is a plan view of the lamp house.
FIG. 11 is a sectioned view in direction C—C' in FIG. 10.
FIG. 12 is a view as seen in arrow direction D—D' in FIG. 10.
FIG. 13 is a sectioned view in direction E—E' in FIG. 10.
FIG. 14 is a perspective view of a heat sink.
FIG. 15 is an explanatory view of a method of fixing the heat sink and lamp house.

FIG. 16 is an explanatory view of fixing a light source to the heat sink.

FIG. 17 is a sectioned view of the heat sink to which the light source is fixed.

FIG. 18 is a perspective view of a fan nozzle.

FIG. 19 is a view as seen in arrow direction F in FIG. 18.

FIG. 20 is an explanatory view of fixing the fan nozzle.

FIG. 21 is a sectioned view of a lamp house.

FIG. 22 is a sectioned view in direction G—G' in FIG. 21.

FIG. 23 is an explanatory view of a method of fitting an infrared ray cutting filter.

FIGS. 24(a) to (c) are explanatory views of a cooling fan.

FIG. 25 is an explanatory view of an opening and closing part.

FIG. 26 is a perspective view of the opening and closing part.

FIG. 28 is a perspective view of the opening and closing part.

FIGS. 29 to 31 relate to the fourth embodiment of the present invention.

FIG. 29 is an explanatory view of an opening and closing part.

FIG. 30 is a sectioned view of the opening and closing part.

FIGS. 31(a) and (b) are explanatory views of a size of a mesh of a screen and a size of an opening.

FIGS. 32 to 34 relate to the fifth embodiment of the present invention.

FIG. 32 is an explanatory view of an opening and closing part.

FIGS. 33(a)-33(b) explanatory views of an illuminating light emitting window of an inner case.

FIGS. 34(a) to (c) are views showing the position relations of a lamp and an opening and closing door within a light source apparatus.

FIG. 37 is an explanatory view of an opening and closing part.

FIG. 38 is a sectioned view of the opening and closing part.

FIG. 39 is a schematic formation view of a light source part.

FIG. 40 is a circuit diagram of a light source apparatus.

DETAILED DESCRIPTION OF THE PREFERRED EMBODIMENTS OF THE INVENTION

The embodiments of the present invention shall be explained in the following with reference to the drawings.

FIGS. 4 to 24 show the first embodiment of the present invention.

In this embodiment, the present invention is applied to an endoscope apparatus and the electromagnetic wave noise generating source is a lamp outputting an illuminating light.

Figure 4:
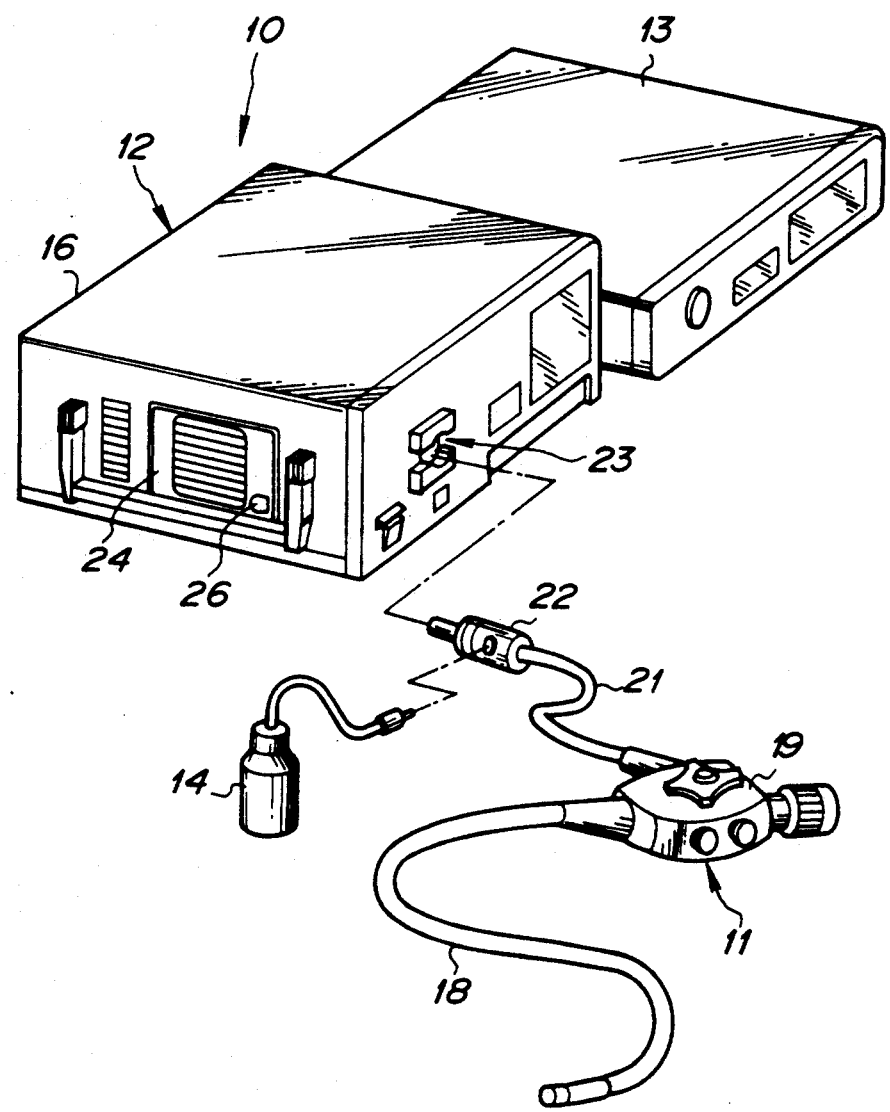

In FIG. 4, the endoscope apparatus 1 of this embodiment comprises an endoscope (which shall be called a fiber scope hereinafter, but is not limited thereto and may be an electronic scope 11, a light source apparatus 12 feeding an illuminating light to the fiber scope 11, a camera controlling unit 13 used in case an externally fitted television camera (not illustrated) is fitted to the fiber scope and a water feeding tank 14.

The above mentioned fiber scope 11 is provided with a thick operating part 19 connected to an elongate insertable part 18 in the rear and a universal cord 21 extended from the side of the operating part 19. The universal cord 21 is provided at the rear end with a light source connector 22 which is to be connected to a connector receptacle 23 provided on the front surface of the above mentioned light source apparatus 12 and is to be fed with an illuminating light output from a lamp 17 which is an electromagnetic wave noise generating source and is housed within the light source apparatus 12.

An opening and closing door 24 is provided on the side wall of a case 16 forming the above mentioned light source apparatus 12 and formed of an electroconductive material and can be opened and closed by the operation of a locking mechanism 26 so that an internal member as the above mentioned lamp 17 housed in the case 16 may be replaced.

Figure 5:
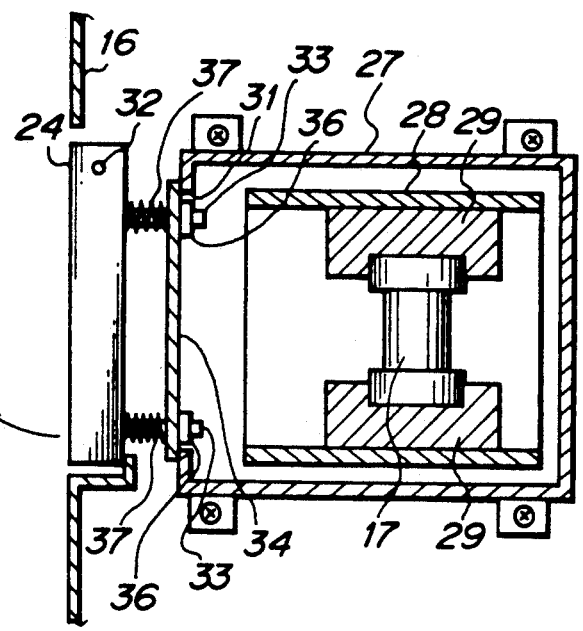
Figure 6:
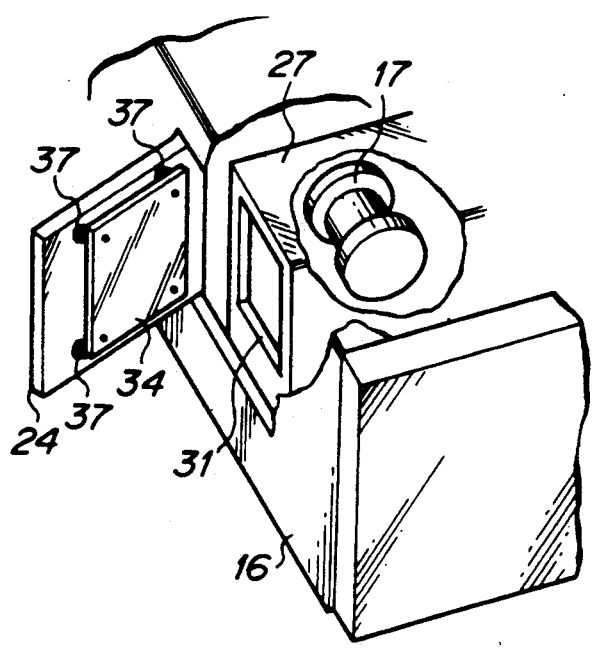

In FIGS. 5 and 6, the above mentioned lamp 17 is held by heat sinks 29 as cooling members within a lamp house 28 which is enclosed with an inner case 27 formed of a conductive material such as a metal. This inner case 27 is provided with an opening 31 in a position facing the above mentioned opening and closing door 24 and is fixed within the above mentioned case 16 so as to be conductive with the case 16.

The above mentioned opening and closing door 24 is held by the case 16 so as to be free to open and close through a rotary shaft 32 and is provided on the inside surface with, for example, four pins 33 formed of an electroconductive material to project on the lamp 17 side. These pins 33 are respectively passed through holes made in the four corners of an inner door 34 formed to be like a square plate of an electroconductive material such as a metal, are fixed at the tips with E-rings as locking members and are further provided with coil springs 37 as pressing members between the opening and closing door 24 and inner door 34 so that the inner door 34 may be pressed against the above mentioned E-rings.

When the above mentioned opening and closing door 24 is closed, the inner door 34 will close the opening 31 of the inner case 27, the inner door 34 and inner case 27 will be conductive with each other and further the inner door 34, opening and closing door 24 and case 16 will be conductive with one another to completely enclose the lamp 17.

Figure 7:
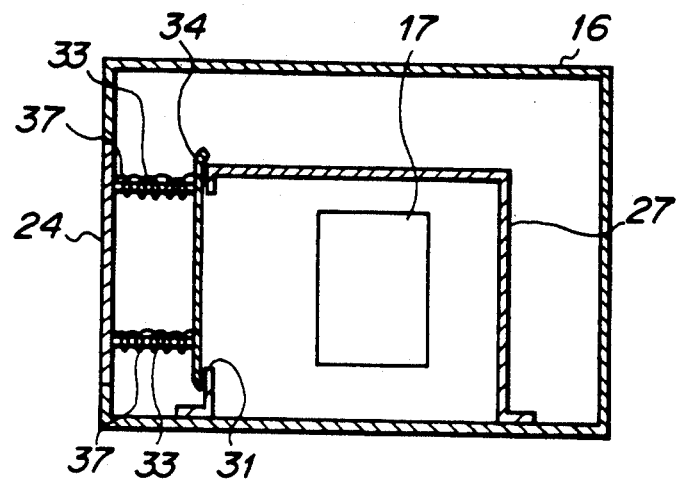
Figure 8:
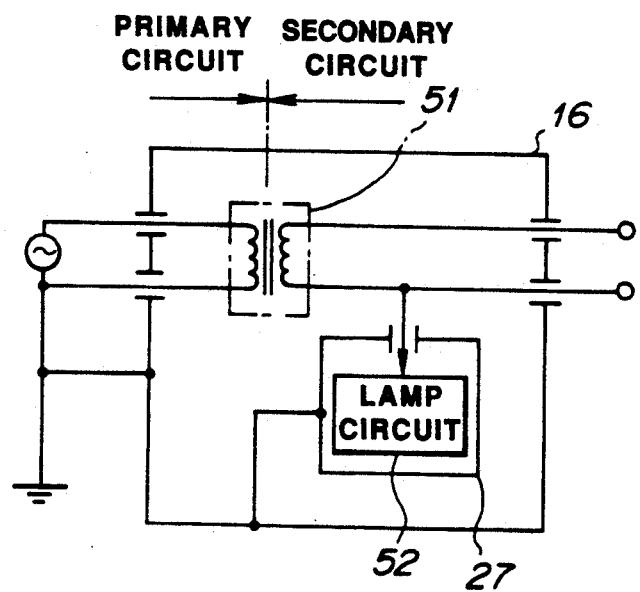

The electric state shall be explained by using FIGS. 7 and 8. In FIG. 7, the inner case (shielding box) 27 is fixed directly to the case 16 and is electrically conductive. The inner door 34 is conductive with the case 16 by the pins 33. They are as shown in a circuit diagram in FIG. 8. In order to secure safety, the circuit within the light source apparatus 12 is electrically separated by a transformer 51 into a primary circuit and secondary circuit. The inner case (shielding box) 27 is connected with the case 16, that is, the primary circuit by being fixed directly with the pins 33 and the case 16 is grounded. A lamp circuit 52 including the lamp 17 connected to the secondary circuit within the inner case 27 is electrically floating.

In this embodiment, when replacing the lamp 17, when the opening and closing door 24 is open, the inner case 34 will be also simultaneously opened. The lamp 17 is taken out through the opening 31 and instead a new lamp 17 is fitted therein.

When the replacement ends and the opening and closing door 24 is closed, the inner door 34 will simultaneously close the opening. When closed, the inner door 34 will contact the inner case 27. The inner door 34 will be pressed by the coil springs 37 against the inner case 27 to completely enclose the lamp 17 together with the inner case 27 and the inner door 34 and inner case 27 will be electrically conductive with each other.

In such a state, electromagnetic wave noise discharged out of the lamp 17 will be grounded through the inner case 27, inner door 34 and pins 33 or directly by being dropped to the case 16 from the inner case 27.

According to this embodiment, as the electromagnetic wave noise generating lamp 17 is provided within the inner case 27 and further the opening 31 provided in the inner case 27 to replace the lamp 17 can be closed with the inner door 34, the electromagnetic wave noise will be grounded through the inner case 27, inner door 34 and pins 33 or directly by being dropped to the case 16 from the inner case 27 and therefore will have no bad influence on other electric devices and circuits.

Also, in the used state, the inner door 34 and the like will be hidden within the case 16 and therefore the appeance will not be impaired.

Further, in such a medical device as the light source apparatus 12 described in this embodiment, it is necessary to secure electric safety by separating the primary circuit and secondary circuit from each other. In such a formation as is mentioned above, when the primary circuit and secondary circuit are separated from each other to secure safety, the radiation of electromagnetic wave noise will be able to be reduced.

Further, when the lamp 17 which is an electromagnetic wave noise generating source is enclosed with the inner case 27 and inner door 34 within the case 16, the influence of the electromagnetic wave noise on the other circuits of the case 16 will be able to be reduced.

The above mentioned lamp house 28 may be formed as shown in FIGS. 9 to 24.

The formation of the lamp house 28 shall be explained in the following.

Figure 9:
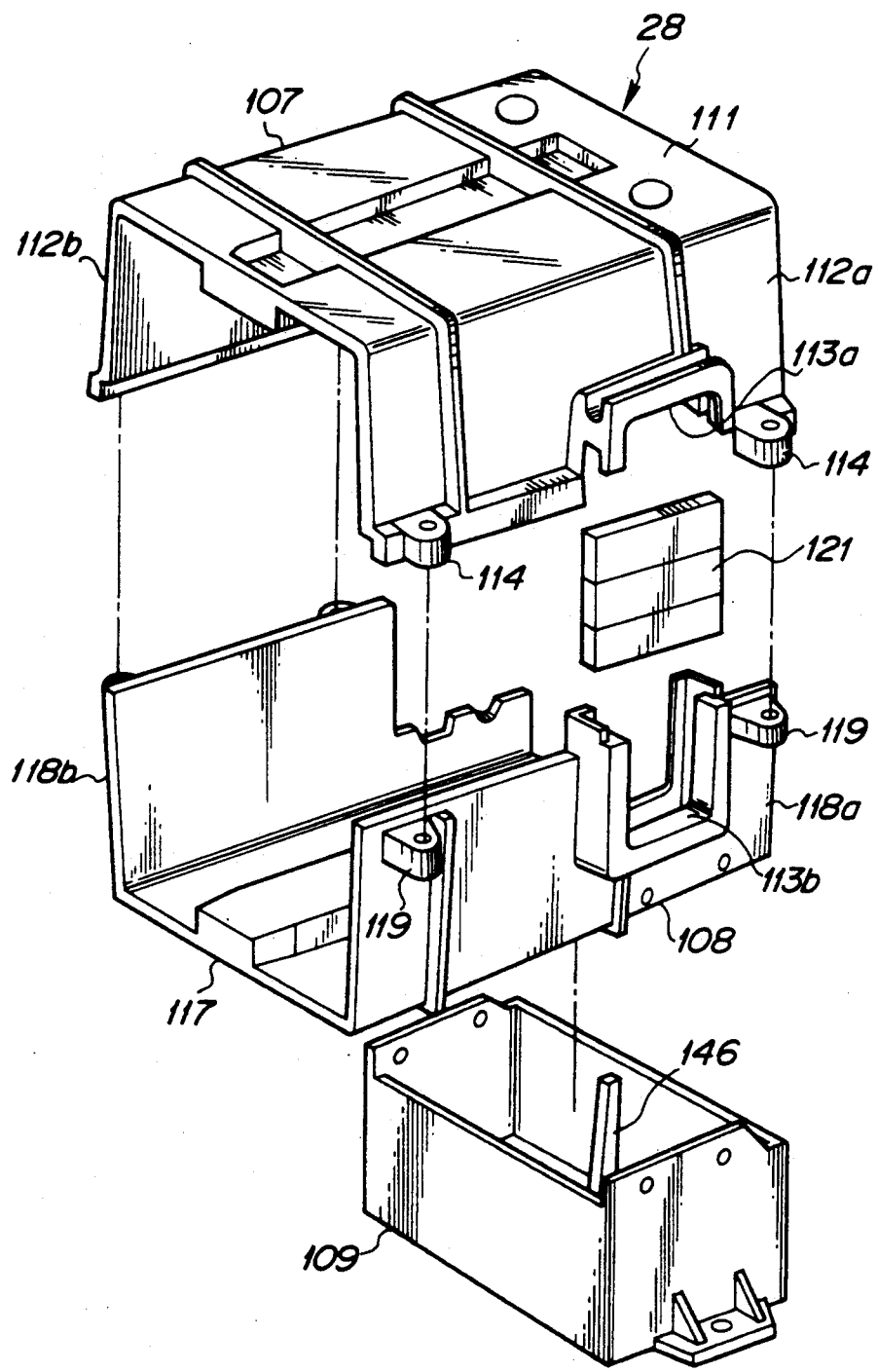
Figure 10:
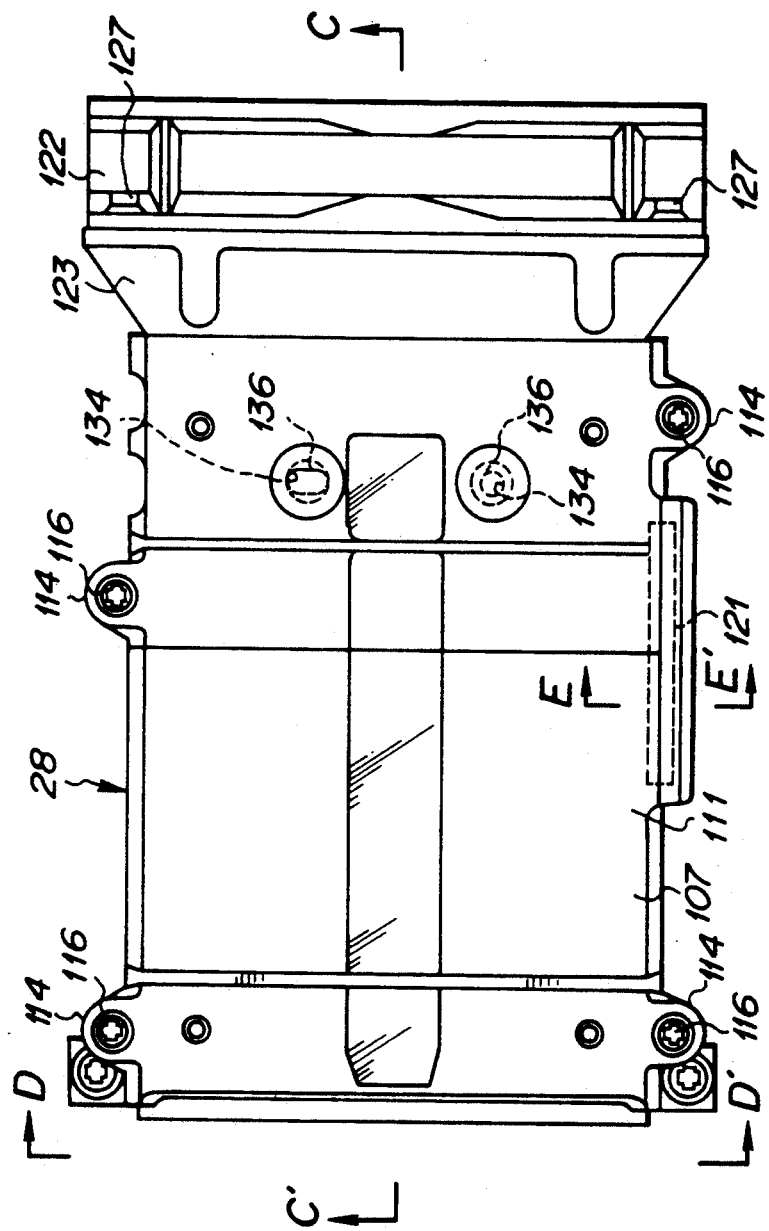

As shown in FIG. 9, the lamp house 28 comprises an upper lamp house 107, a lower lamp house 108 and a substrate housing case 109.

The above mentioned upper house 107 is formed of a top plate 111 and side plates 112a and 112b so as to have a substantially U-like cross-section. One side plate 112a is partly incised on the lower edge to form an upper filter window 113a. Also, the above mentioned lower lamp house 108 is formed to have the same substantially U-like cross-section with a bottom plate 117 and side plates 118a and 118b and is partly incised on the upper edge of one side plate 118a to form a lower filter window 113b.

Figure 13:
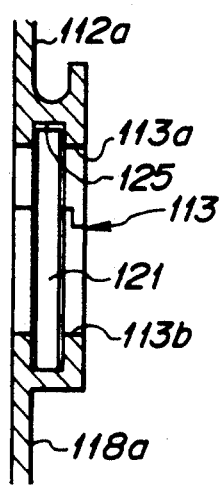

Fixing legs 114 are provided on the lower edges of the above mentioned side plates 112a and 112b and fixed legs 119 are provided in the positions corresponding to the above mentioned fixing legs 114 on the upper edges of the side plates 118a and 118b. Fixing members 116 as, for example, springs are passed respectively through the fixing legs 114 and are screwed respectively into the fixed legs 119 to fix the upper lamp house 107 and lower lamp house 108 to each other. In case the lamp house 28 is integrally assembled, it will be like a box opened at both ends. Also, as assembled, the upper filter window 113a and lower filter window 113b will form one filter window 113 as shown in FIG. 13. An infrared ray cutting filter 121, removing infrared rays from the illuminating light by using a groove 125 as a guide, is provided within this filter window 113.

Figure 18:
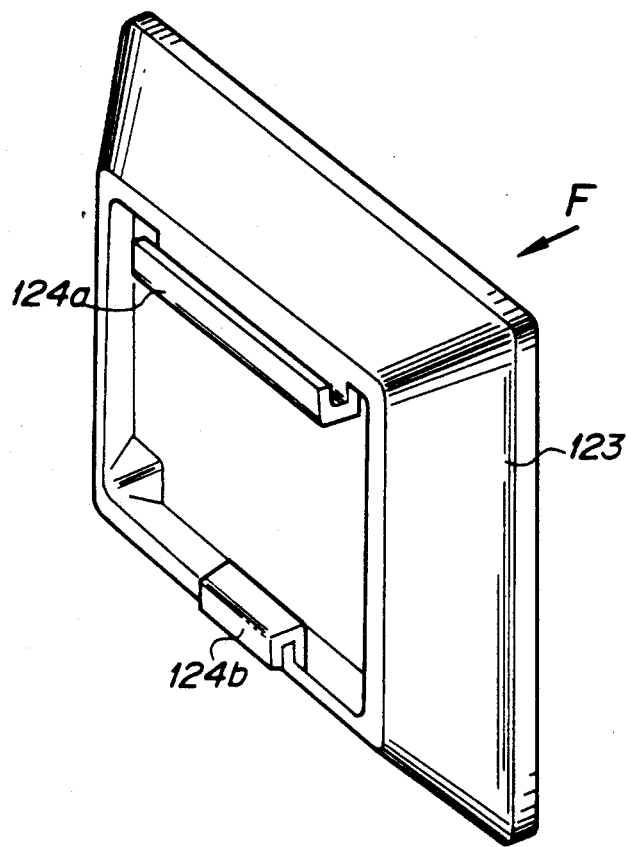
Figure 19:
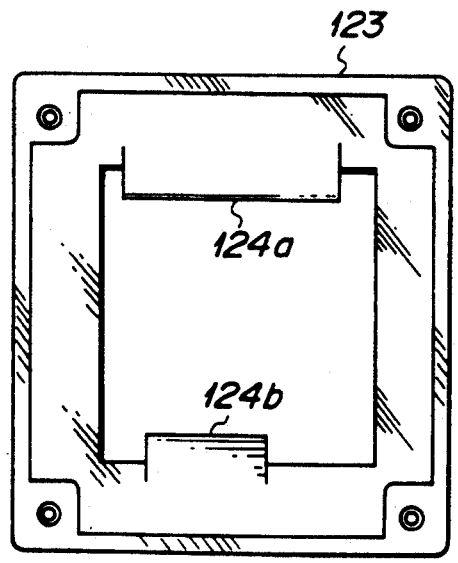

A fan nozzle 123 for holding a cooling fan 122 is provided on one opening side of the above mentioned lamp house 28. The cooling fan 122 is square and is larger in contour than the lamp house 28. The fan nozzle 123 is like a frame expanding from one end to the other end as shown in FIGS. 18 and 19. The fan nozzle 123 is square substantially the same as the contour of the lamp house 28 at one end and is square substantially the same as in the above mentioned cooling fan 122 at the other end. An upper engaged part 124a and lower engaged part 124b are formed respectively above and below one end square substantially the same as in the lamp house 28. The upper engaged part 124a is fitted to an engaging part 126a provided in the upper lamp house 107 and the lower engaged part 124b is fitted to an engaging part 126b provided in the lower lamp house 108 so as to be held when respectively fixing the upper lamp house 107 and lower lamp house 108. The cooling fan 122 and fan nozzle 123 are fixed by fixing members 127 such as screws.

Figure 11:
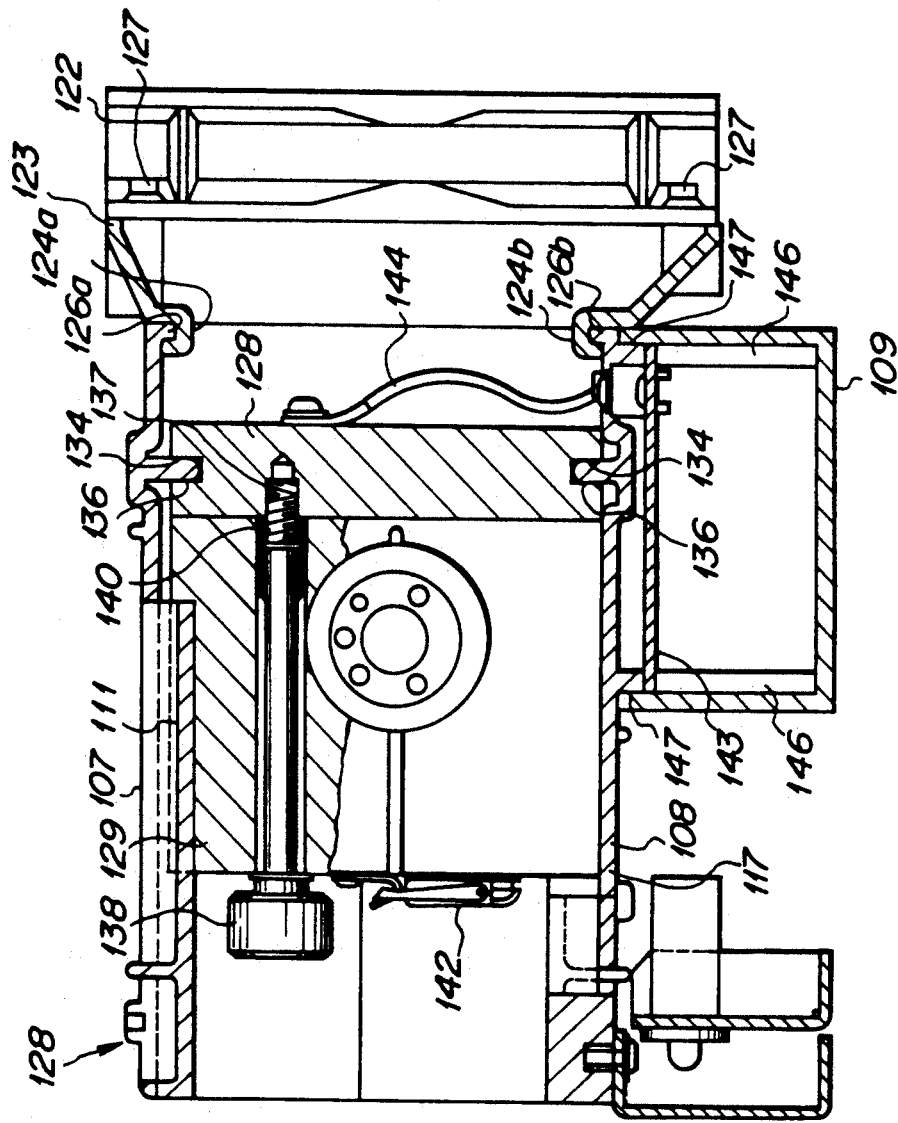
Figure 12:
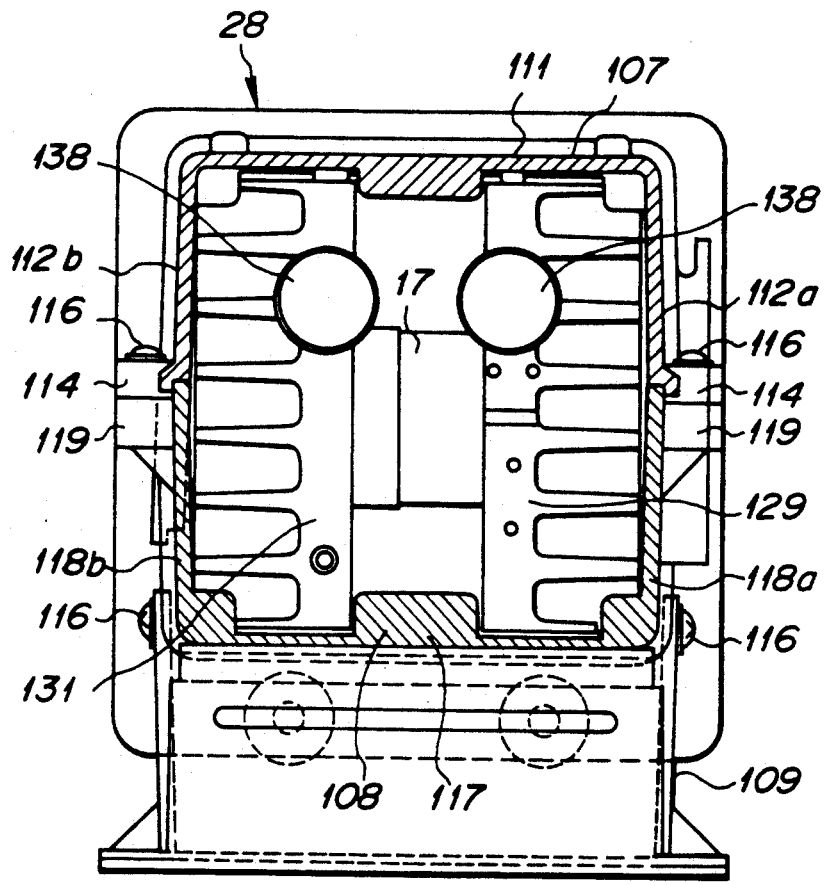
Figure 14:
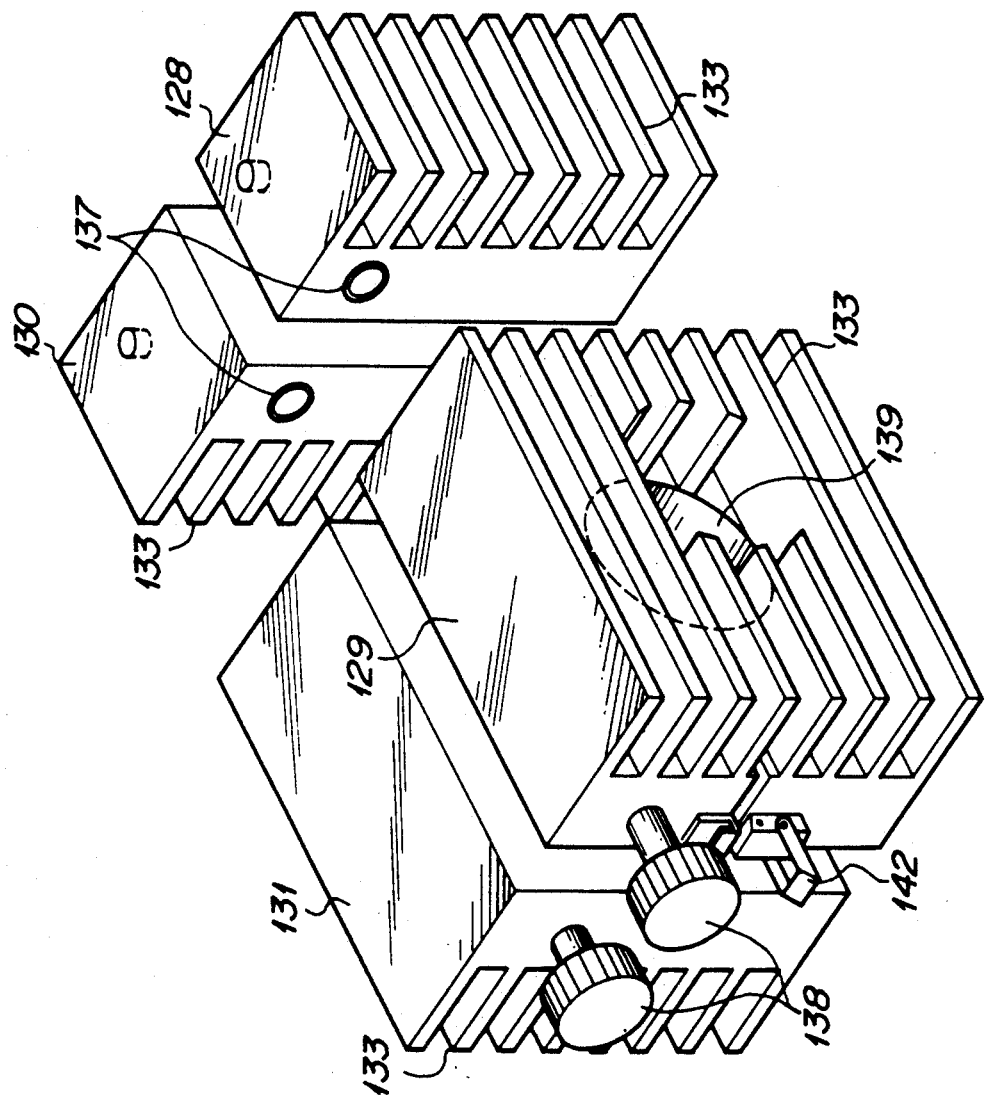
Figure 15:
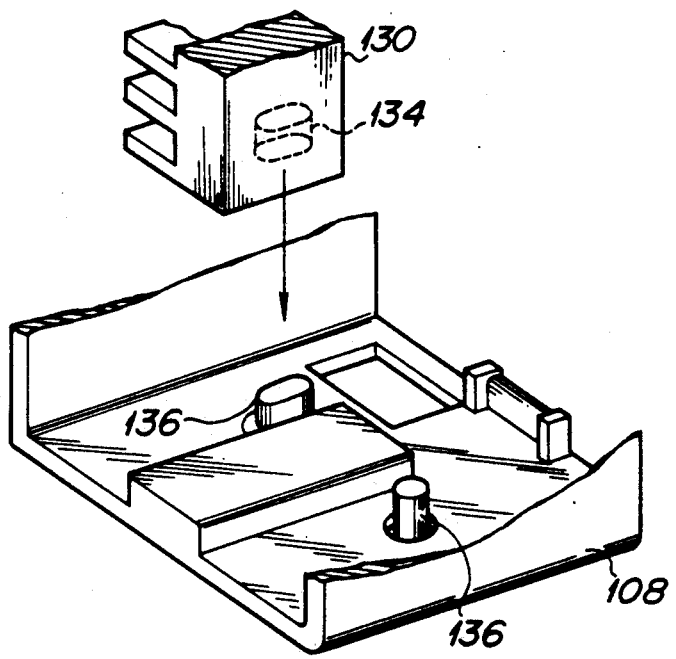

Heat sinks 128, 129, 130 and 131 shown in FIG. 14 are provided in two rows within the above mentioned lamp house 28 to radiate heat generated when a lamp 17 is lighted. One row is provided with the heat sink 128 on the cooling fan side and with the heat sink 129 on the counter cooling fan side. The other row is provided with the heat sink 130 on the cooling fan side and with the heat sink 131 on the counter cooling fan side. The respective rows of the heat sinks 128, 129 and 130, 131 are formed to be symmetrical with each other and a plurality of cooling fins 133 are provided from the cooling fan side toward the counter cooling fan side. The heat sinks 128 and 130 on the cooling fan side are locked respectively to the upper and lower lamp houses 107 and 108. The heat sinks 129 and 131 are fixed by screws to the heat sinks 128 and 130. That is, recesses 134 as are shown in FIGS. 11 and 15 are provided respectively on the upper surfaces and lower surfaces of the cooling fan side heat sinks 128 and 130. Projections 136 are provided in the positions corresponding to the recesses 134 on the inner walls of the upper and lower lamp houses 107 and 108 so that the projections 136 may fit respectively in the recesses 134. The recesses 134 provided in the heat sink 130 and the projections 136 to be fitted respectively in these recesses are made elliptic so as to prevent the rotation of the heat sink 130.

Female screw parts 137 are provided on the counter cooling fan side end surfaces of the cooling fan side heat sinks 128 and 130 so that, when male screw parts 140 of grips 138 passing through the heat sinks 129 and 131 from the counter cooling fan side are screwed respectively into these female screw parts 137, the heat sink 128 may fix the heat sink 129 and the heat sink 130 may fix the heat sink 131.

Figure 17:
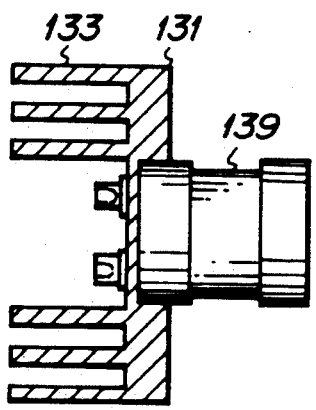
Figure 16:
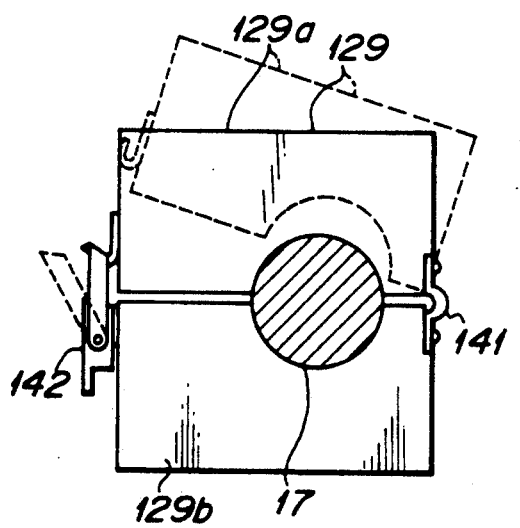

A lamp 17 is provided so as to be able to emit to the heat sinks 129 and 131 an illuminating light through the above mentioned infrared ray cutting filter 121. That is, as shown in FIG. 16, the heat sink 129 is divided into an upper heat sink 129a and lower heat sink 129b which are connected with each other through a plate spring 141. A latch 142 is provided on the other side so as to latch the upper and lower heat sinks 129a and 129b and to hold the lamp 17 at one side end. When latched with the latch 142, the plate spring 141 will be energized and, when unlatched, the upper and lower heat sinks 129a will be opened by the energizing force of the plate spring 141. The lamp 17 is fixed at the other end to the heat sink 131 as shown in FIG. 17.

The above mentioned substrate housing case 109 is fixed to the bottom plate 117 of the lower lamp house 108. A substrate 143 fitted with a lighting circuit is arranged within the substrate housing case 109 and is connected with the above mentioned heat sinks 128 and 130 through a connecting terminal 144. The substrate 143 is held horizontal by ribs 146 provided on the inner wall of the case 109 so that, when the case 109 is fitted to the lower lamp house 108, it will be held and fixed by the projections 147 and ribs 146 provided on the bottom plate 117 of the lower lamp house 108.

When assembling the lamp house 28, the heat sinks 128 and 130 are fitted to the lower lamp house 108 so that the recesses 134 of the heat sinks 128 and 130 may fit respectively to the projections 136.

On the other hand, the lamp 17 is fixed at the other end to the heat sink 131 and is held at one end by the upper and lower heat sinks 129a and 129b and is fixed with the latch 142. The integrated heat sinks 129 and 131 and lamp 17 are put into the lower lamp house 108 and the grips 138 are rotated to screw the male screw parts 140 into the female screw parts 137 of the heat sink 128 and 130 so that the heat sinks 129 and 131 and lamp 17 may be fixed to the lower lamp house 108 through the heat sinks 128 and 130.

Figure 20:
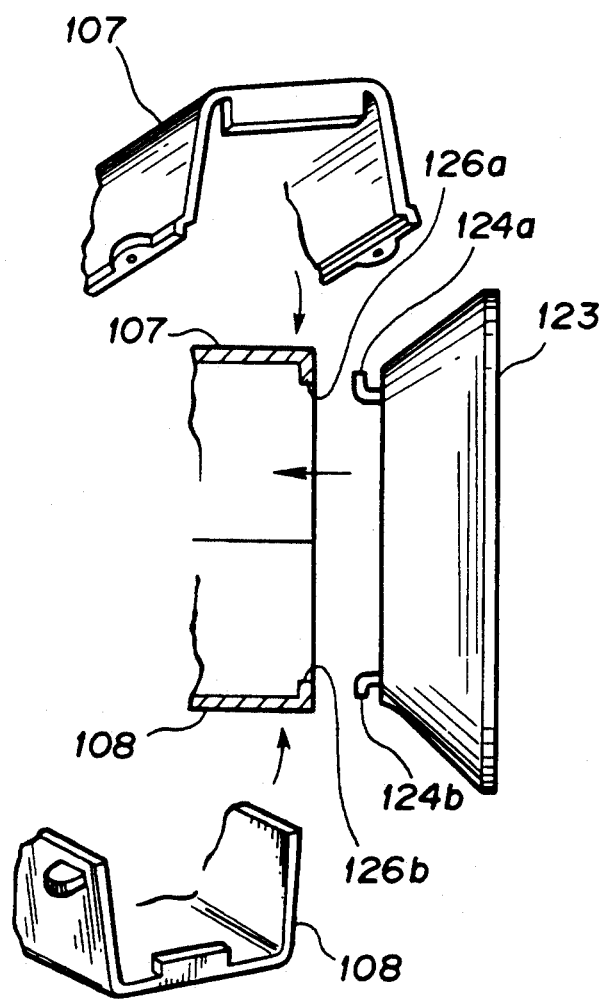
Figure 21:
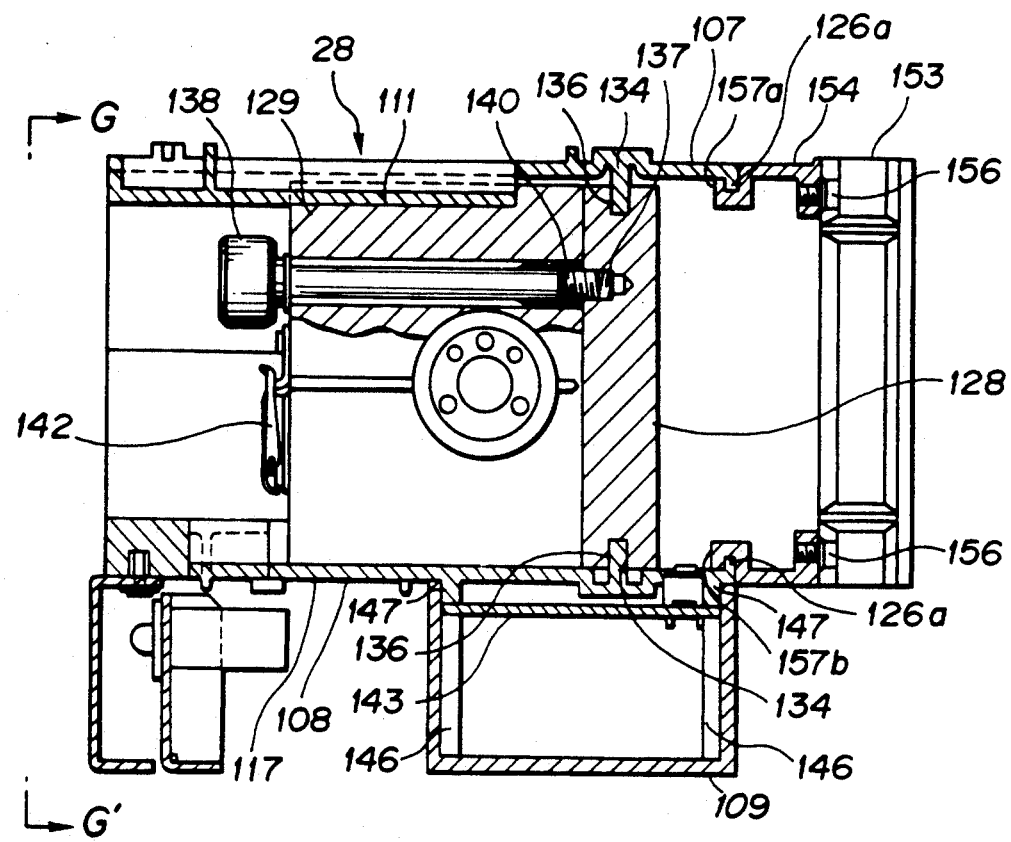
Figure 22:
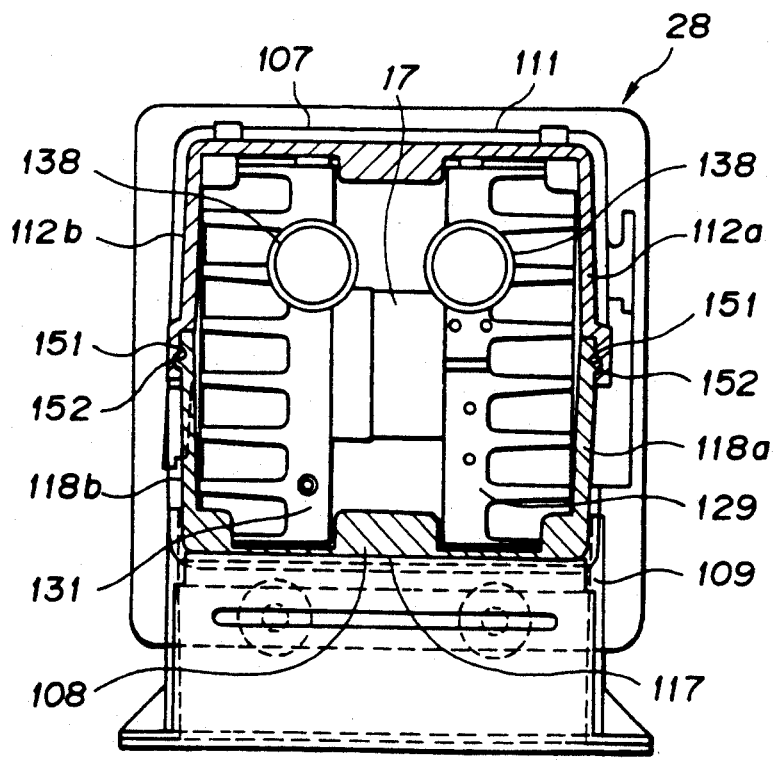

The infrared ray cutting filter 121 is then inserted into the lower filter window 113b with the groove 125 as a guide. The upper lamp house 107 is placed on the lower lamp house so that the engaged part 126b below the fan nozzle 123 fixed with the cooling fan 122 and fixing members 127 may be engaged with the lower engaging part 126 of the lower lamp house 108. The fixing legs 114 and fixed legs 119 are fixed with the fixing member 116. In such a case, when the engaging part 126a of the upper lamp house 107 is engaged with the upper engaged part 124a of the fan nozzle 123 as shown in FIG. 20, the fan nozzle 123 and upper and lower lamp houses 107 and 108 will be simultaneously fixed.

A substrate 143 fitted with a lighting circuit, is then arranged as hung at the end on ribs 146 within the substrate housing case 109 which is fitted to the bottom plate 117 of the lower lamp housing 108 so that the substrate 143 may be held and fixed by the ribs 146 and bottom plate 117.

As the upper lamp house 107 and lower lamp house 108 can be fixed with the fixing members 116 and at the same time the cooling fan 122 can be fitted through the fan nozzle 123 as mentioned above, the assembling members of the parts within the lamp house can be reduced to be less than in separately fitting the cooling fan 122, the operatability and assemblability can be improved and the maintenance in replacing parts in the repair can be improved.

Also, as in FIGS. 21 to 24, the upper lamp house 107 and lower lamp house 108 may be fixed without using the fixing member 116.

In FIGS. 21 to 24, the upper lamp house 107 is formed of an elastic material and recesses 151 are provided near the lower side edges of the side plates 112a and 112b. Projections 152 are provided to be engaged with the above mentioned recesses 151 in the positions corresponding to the above mentioned recesses 151 and near to the upper side edges of the side plates 118a and 118b of the lower lamp house 108.

A fan nozzle of substantially the same square form as the contour of the lamp house 28 is provided in one opening of the lamp house 28. As different from the fan nozzle 123 described in FIGS. 18 and 19, this fan nozzle 154 is not expanded in the openings at both ends but is of the same contour.

The lamp house 28 and fan nozzle 154 are fixed the same as in FIGS. 18 and 19 so that the upper engaged part 157a and lower engaged part 157b provided in the fan nozzle 154 may be simultaneously respectively engaged with the engaging part 126a of the upper lamp house 107 and engaging part 126b of the lower lamp house 108 when fitting the upper lamp house 107 to the lower lamp house 108. A cooling fan 153 of a wind volume smaller than of the cooling fan described in FIGS. 18 and 19 and substantially the same contour as the lamp house 28 is fixed by fixing members 156.

The other formations are the same as of the lamp house 28 described in FIGS. 9 to 20.

In the lamp house 28 described in FIGS. 21 to 24, in fixing the upper lamp house 107 to the lower lamp house 108, the upper lamp house 107 is elastically transformed in the lower side edge part, the recesses 151 are engaged respectively with the projections 152 and the upper lamp house 107 and lower lamp house 108 are fixed by the energizing force so that the upper and lower lamp houses 107 and 108 may be easily assembled and disassembled without using the fixing member 116.

In case the lamp 17 is of a lighting type, the heat generation will be less than in a flash type and therefore a cooling fan 153 of a wind volume smaller than of the cooling fan 122 described in FIGS. 9 to 20 is provided as shown in FIG. 24. However, in such a case, by using a fan nozzle 154, the cooling fan 153 can be fitted to the lamp house 28. Therefore, by selecting the fan nozzle in conformity with the size of the cooling fan, cooling fans of various contours can be fitted without modifying the lamp house 28.

As shown in FIG. 23, the infrared ray cutting filter 121 may be fitted to the lamp house 28.

In FIG. 23, the infrared ray cutting filter 121 is held by a filter frame 158. A fixing hole 161 through which a screw 159 is passed is provided above the filter frame 158. Below the filter frame 158, an engaging projection 162 is provided to project downward.

On the other hand, a hole 163 into which the above mentioned screw 159 is to be screwed is provided above the upper filter window 113a of the upper lamp house 107 and a projection receptacle 164 to be engaged with the above mentioned engaging projection 162 is provided below the lower filter window 113b of the lower lamp house 108. In FIG. 23, the filter frame 158 having the infrared ray cutting filter 121 is fitted to the filter window 113 by engaging the engaging projection 162 with the projection receptacle 164 and screwing the screw 159 into the screw hole 163 through the fixing hole 161.

The above mentioned fan nozzles 123 and 154 are fitted with the cooling fans 122 and 153 of a contour which is the same as or larger than the lamp house 28 but may be made smaller in contour to fit cooling fans of a contour smaller than the lamp house 28.

The endoscope apparatus 10 of this embodiment comprises a light source apparatus 12, fiber scope 11, externally fitted camera, camera controlling unit 13 and water feeding tank 14 but may also comprise a video scope, camera controlling unit and scope cable connecting the video scope and camera controlling unit.

Figure 25:
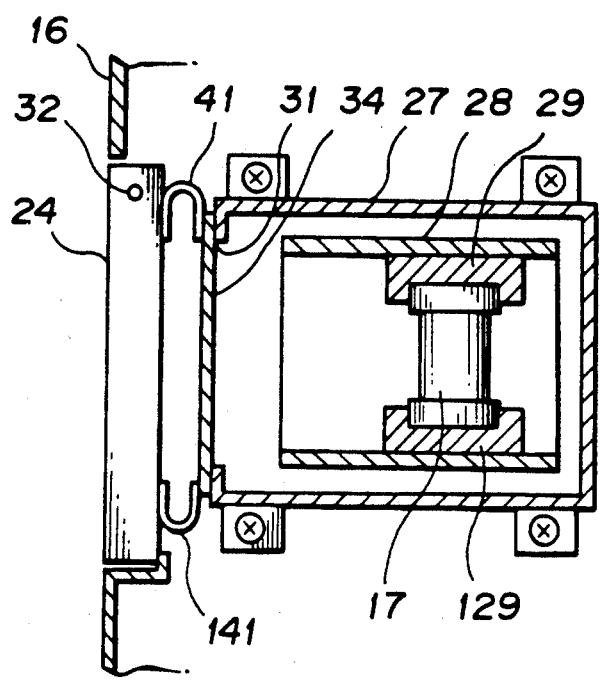
FIGS. 25 and 26 relate to the second embodiment of the present invention.
Figure 26:
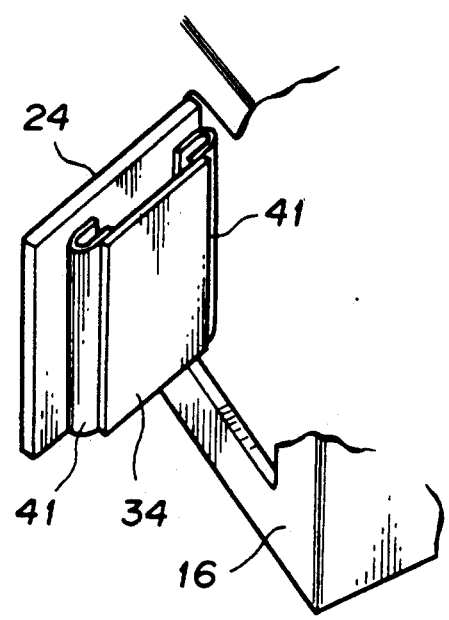

FIGS. 25 and 26 show the second embodiment of the present invention.

The same component members as in the first embodiment shall bear the same reference numerals and shall not be explained here.

In this embodiment, a U-like plate spring 41 is provided in place of the coil spring 37 in the first embodiment.

An opening and closing door 24 in this embodiment is provided on the inside surface with plate springs 41 as closing members formed to be U like of an electroconductive material and further at the ends of these plate springs at the side of lamp 17, an inner door 34 is formed to be square and of an electroconductive material such as a metal so that, when the opening and closing door 24 is closed, this inner door 34 will be pressed against the inner case 27 by the plate springs 41 to completely close the opening 31.

In this embodiment, when the opening and closing door 24 is closed, the inner case 27 and inner door 34 will enclose the lamp 17 and will be conductive through the plate springs 41 and the electromagnetic wave noise radiated from the lamp 17 will be grounded through the inner case 27, inner door 34 and plate springs 41 or directly by being dropped to the case 16 from the inner case 27.

The other formations, operations and effects are the same as in the first embodiment.

Figure 27A:
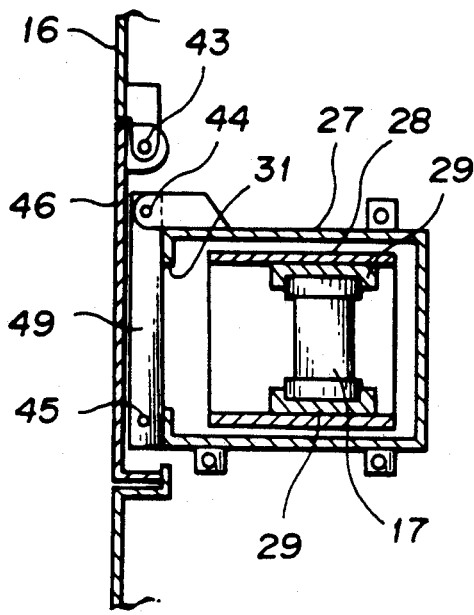
FIGS. 27(a) and (b) are explanatory views of an opening and closing part.
Figure 27B:
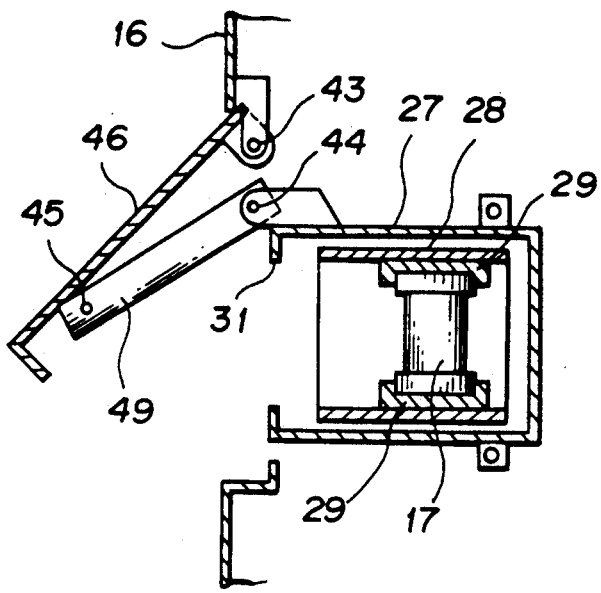
FIGS. 27 and 28 relate to the third embodiment of the present invention.
Figure 28:
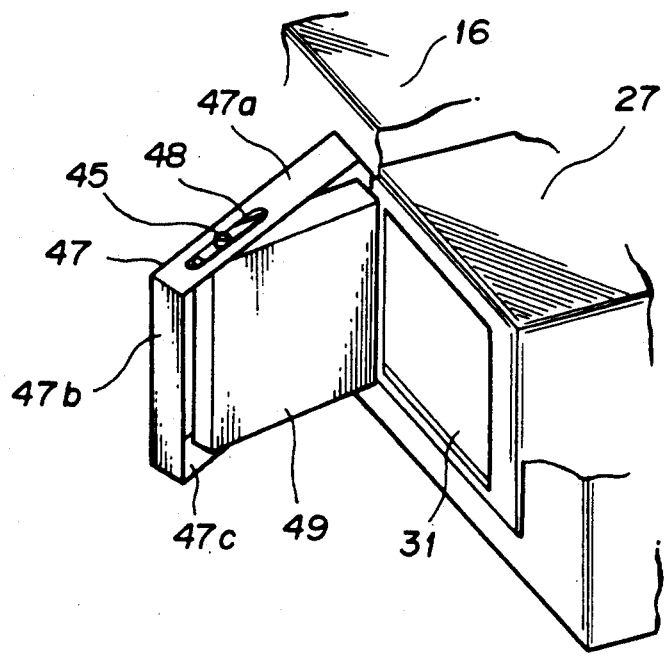

FIGS. 27 and 28 show the third embodiment of the present invention.

The same component members as in the first embodiment shall bear the same reference numerals and shall not be explained here.

An opening and closing door 46 in this embodiment is held by the case 16 so as be free to open and close through a rotary shaft 43. An upper flange 47a, side flange 47b and lower flange 47c are extended inward on the peripheral edge of this opening and closing door 46. The upper flange 47a is provided along the edge with an elliptic cam groove 48 along the edge of the flange 47a. The inner door 49 is held on one end side by a rotary shaft 44 provided on the inner case 27 so as to be free to open and close and is provided on the other end side with a pin 45 to be engaged with the above mentioned cam groove 48. The inner door 49 and pin 45 are made of an electroconductive material.

In this embodiment, when the opening and closing door 46 is opened, the pin 45 provided on the inner door 49 will be pulled while sliding within the cam groove 48 so that the inner door 49 may open as shown in FIG. 27(b). When the opening and closing door 46 is closed, in the same manner, the pin 45 will slide within the cam groove 48 and the inner door 49 will close as shown in FIG. 27(a).

In this embodiment, when the opening and closing door 46 is closed, the inner door 49 and inner case 27 will be conductive and the inner door 49 together with the inner case 27 will enclose the lamp 17 which is a noise generating source. Therefore, the electromagnetic wave noise generated in the lamp 17 will be grounded through the inner door 49 and pin 45 or directly by being dropped to the case 16 from the inner case 27.

The other formations, operations and effects are the same as in the first embodiment.

FIGS. 29 to 31 show the fourth embodiment of the present invention.

In this embodiment, an inner door 34 is provided with a net formed of an electroconductive material.

An opening and closing door 24 in this embodiment has in the central part on the inside surface the same opening as an opening 31 provided on the inner case 27 and is provided with a holding member 54 formed to be like a plate of an electroconductive material and fixed by fixing legs 54a provided in the four corners. The holding member 54 is provided on the periphery of the end surface on the side of the inner case 27 with an electroconductive finger member 4 shown in FIG. 3 so that, when the opening and closing door 24 is closed, the electroconductive finger member 4 will be transformed to contact the inner case 27.

The opening of the above mentioned holding member 54 is covered with a net 56 formed of an electroconductive material. The size B of the mesh of the net 56 shown in FIG. 31(a) is made smaller than the wavelength of the electromagnetic waves to be reduced. Also, in case a punched metal 57 with many holes 57a as shown in FIG. 31(b) is used in place of the net 56, the size B of the opening of the hole 57a will be made smaller than the wavelength of the electromagnetic waves to be reduced. When the size B of the mesh of the net 56 or the opening of the hole 57a is thus set, the shielding of electromagnetic wave noise will be able to be made on a level having no problem as compared with a metal sheet. In this embodiment, the inner door 34 is formed of the holding member 54, electroconductive finger member 4 and net 56.

The above mentioned opening and closing door 24 is provided with a vent 58 in the position facing the opening provided in the holding member 54 so that air having cooled the interior of the inner case 27 may be discharged out through the vent 58, opening of the holding member 54 and opening 31 of the inner case 27.

In this embodiment, when the opening and closing door 24 is closed, the inner door 34 and inner case 27 will be conductive with each other through the electroconductive finger member 4 so that the electromagnetic wave noise will be grounded through the inner case 27, inner door 34 and fitting legs 54a or directly by being dropped to the case 16 from the inner case 27.

The other formations, operations and effects are the same as in the first embodiment.

Figure 32:
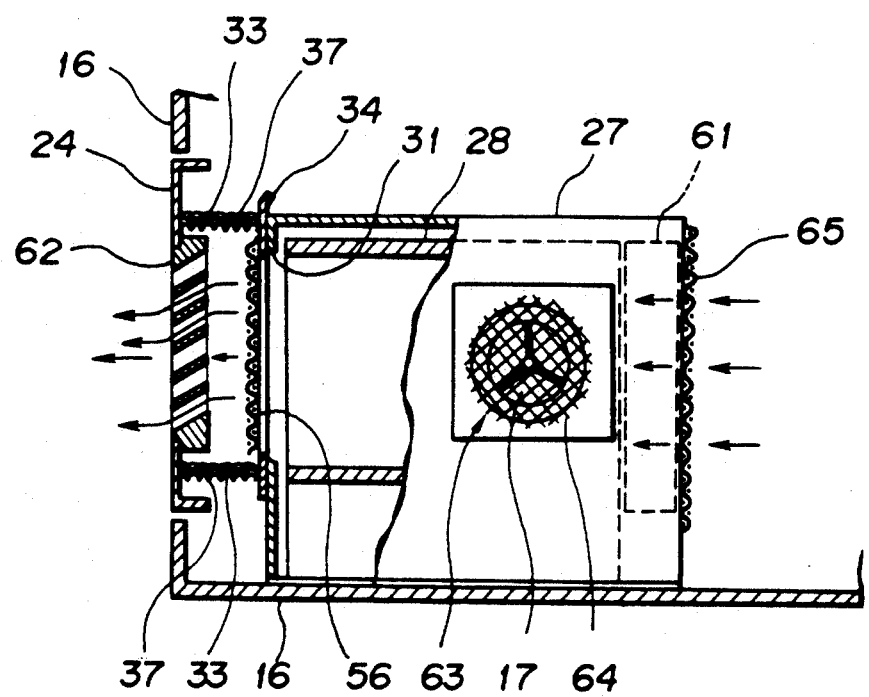

FIGS. 32 to 34 show the fifth embodiment of the present invention.

In this embodiment, the electroconductive finger member 4 is removed from the formation of the fourth embodiment and instead the pins 33, E-rings 36 and coil springs 37 described in the first embodiment are provided so that, in case the opening and closing door 24 is closed, the opening 31 of the inner case 27 will be closed.

In this embodiment, in addition to the formation of the fourth embodiment, the lamp house 28 is provided with a cooling fan 61 for cooling the lamp 17. The cooling fan 61 is provided to face the opening 31 of the inner case 27 so that air may be taken into the inner case to cool the lamp 17 and may be discharged out through the opening 31, an opening provided in a holding member 54 and a lattice-like venting member 62 provided in the opening and closing door 24. The air intake port of the cooling fan 61 is covered with a net 65 formed of an electroconductive material so as to reduce the radiation of electromagnetic wave noise. The arrows in FIG. 32 show the flow of air.

As shown in FIGS. 32 and 33, an illuminating light emitting window 63 for emitting the illuminating light generated by the lamp 17 is provided on the inner case 27 and is covered with a net 64 formed of an electroconductive material of a transmissivity above 90%. This net 64 formed of an electroconductive material conducts with the inner case 27 so as to reduce the electromagnetic wave noise radiated out of the inner case 27.

In consideration of the replacing ease and operatability, the lamp 17 or any other electromagnetic wave generating source required to be replaced is set near the opening and closing door 24 side as shown in FIG. 34 so that the maintainability may be elevated. Also, as it is located not in the center but at the end within the case 16, its negative influence on other mechanisms and circuits can be reduced.

FIG. 34(a) is a plan view of a light source apparatus.
FIG. 34(b) is an elevation of the light source apparatus.
FIG. 34(c) is a side view of the light source apparatus.

The other formations, operations and effects are the same as in the first embodiment.

Figure 35:
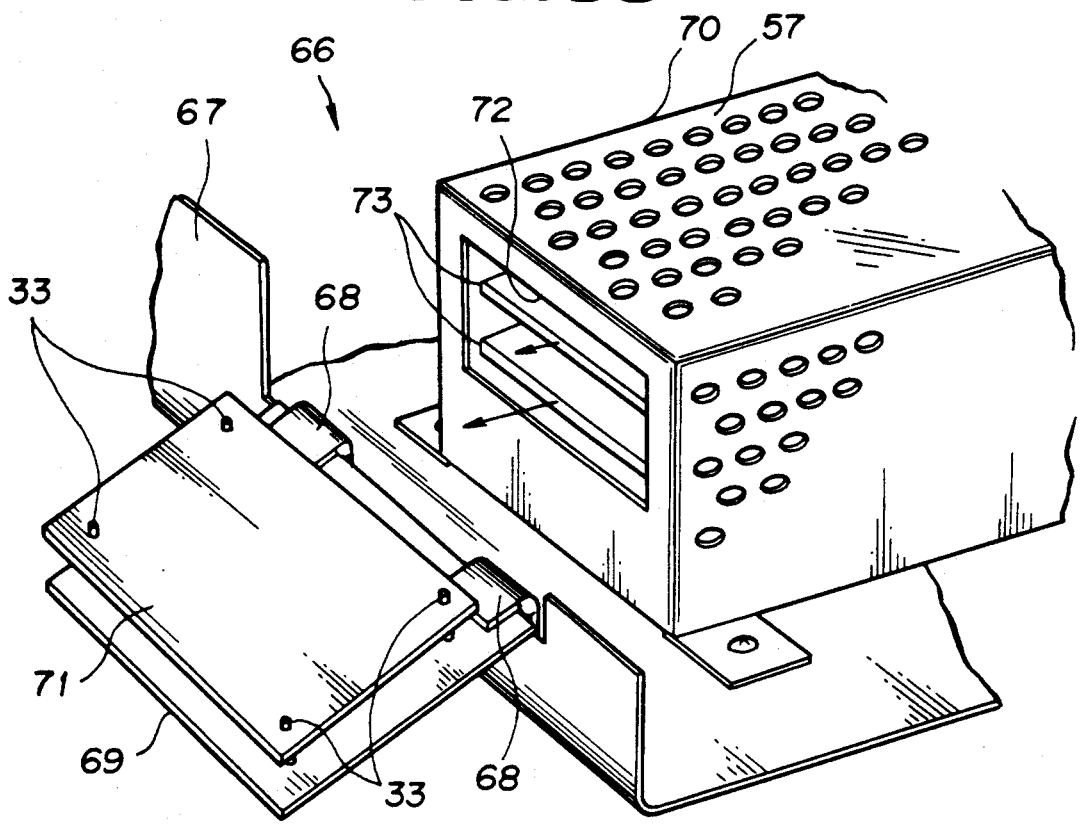
FIG. 35 relates to the sixth embodiment of the present invention and is an explanatory view of an opening and closing part.

FIG. 35 shows the sixth embodiment of the present invention.

In this embodiment, the present invention is applied to an electric apparatus housing a substrate fitted with an electromagnetic wave generating source.

In an electric apparatus 66 of this embodiment, a case 67 is provided with an opening and closing door 69 made free to open and close vertically by hinges 68. The opening and closing door 69 is provided on the inner surface with an inner door 71 by the pins 33, E-rings 36 and coil springs 37 described in the first embodiment. The inner door 71 conducts to the case 67 through the pins 33 and opening and closing door 69 the same as in the first embodiment.

Within the above mentioned case 67, an inner case 70 formed of the punched metal 57 explained in FIG. 31(b) is fixed to the case 67 to be conductive with each other. An opening 72 is provided in the position facing the opening and closing door 69 of the inner case 70 so that digital circuit substrates 73 which are housed in the inner case 70 and are electromagnetic wave generating sources may be pulled out in the direction indicated by the arrows in the drawing.

In this embodiment, the same as in the first embodiment, the electromagnetic wave noise generated from the digital circuit substrates 73 are grounded through the inner case 70, inner door 71 and pins 33 or directly by being dropped to the case 67 from the inner case 70.

As mentioned above, in this embodiment, the part likely to break down or be interchanged with another part and required to be replaced can be improved in the maintainability when it is replaced.

Figure 36:
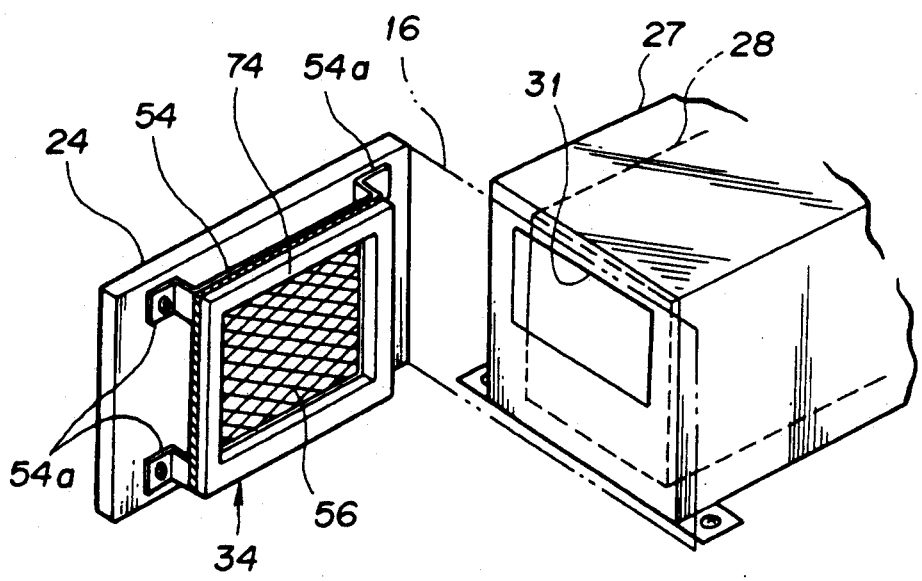
FIG. 36 relates to the seventh embodiment of the present invention and is an explanatory view of an opening and closing part.
Figure 37:
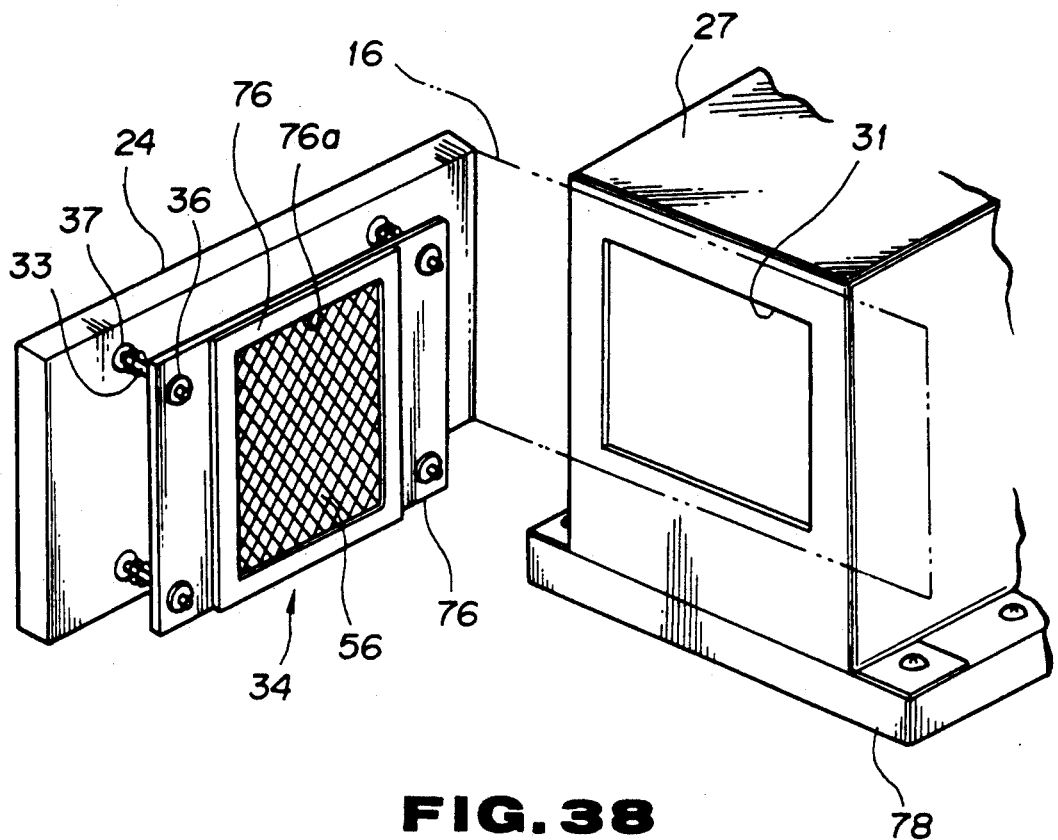
FIGS. 37 to 40 relate to the eighth embodiment of the present invention.
Figure 38:
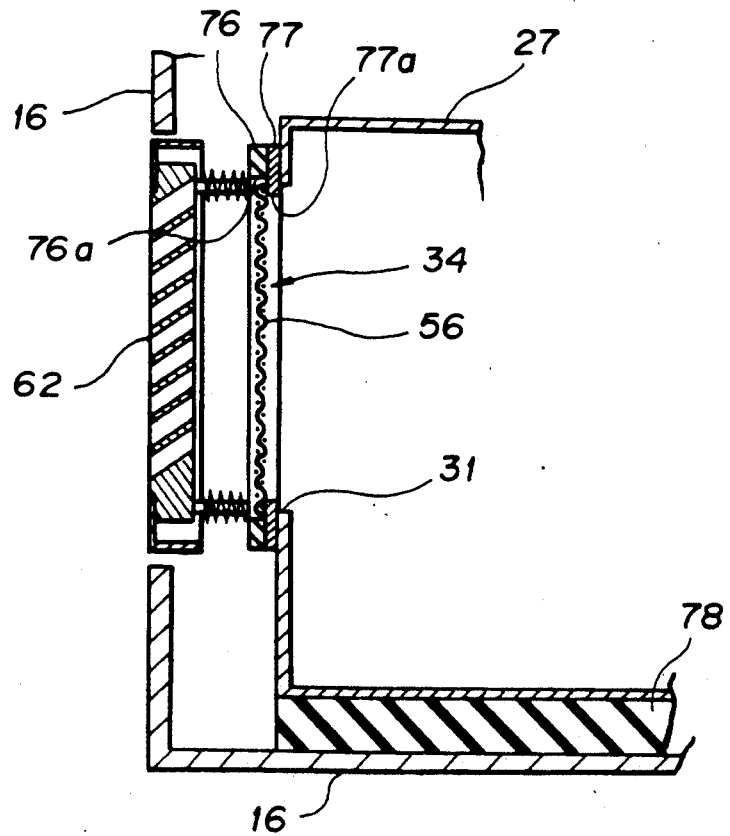

FIG. 36 shows the seventh embodiment of the present invention.

In this embodiment, an electroconductive rubber is used in place of the electroconductive finger member 4 in the fourth embodiment. The same component members as in the first embodiment shall bear the same reference numerals and shall not be explained here.

In this embodiment, an electroconductive rubber 74 containing carbon is provided on the inner surface of the holding member 54 described in the fourth embodiment so as to be pressed against the inner case 27 when the opening and closing door 24 is closed.

In this embodiment, when the opening and closing door 24 is closed, the electroconductive rubber 74 will be pressed against the inner case 27 which will be conductive with the electroconductive rubber 74, holding member 54, net 56, opening and closing door 24 and case 16. As the inner case 27 is immediately fixed to the case 16 to be conductive, the lamp house 28 will be perfectly intercepted from outside and the radiation of electromagnetic wave noise will be able to be reduced.

The other formations, operations and effects are the same as in the first embodiment.

FIGS. 37 to 40 show the eighth embodiment of the present invention.

In the above mentioned respective embodiments, the inner case 27 and case 16 are conductive with each other but, in this embodiment, the inner case 27 and case 16 are insulated from each other. The same component members as in the first embodiment shall bear the same reference numerals and shall not be explained here.

An opening and closing door 24 provided to be free to open and close in the case 16 is fitted with the venting member 62 described in the fifth embodiment and is provided on the inner surface with a holding member 76 formed to be like a plate of an electrically insulating material by the pins 33, E-rings 36 and coil springs 37 described in the first embodiment and having a vent 76a formed in the center. The holding member 76 is fitted on the inner surface with a frame member 77 formed of an electroconductive material and provided with an opening 77a somewhat smaller than the above mentioned vent 76a. The opening 77a of the frame member 77 is provided with a net 56 formed of an electroconductive material to close it.

On the other hand, the inner case 27 is once fixed to a fitting member 78 formed to be like a plate of an insulating material and then the fitting member 78 is fixed to the case 16 to keep the inner case 27 and case 16 insulated from each other.

Figure 39:
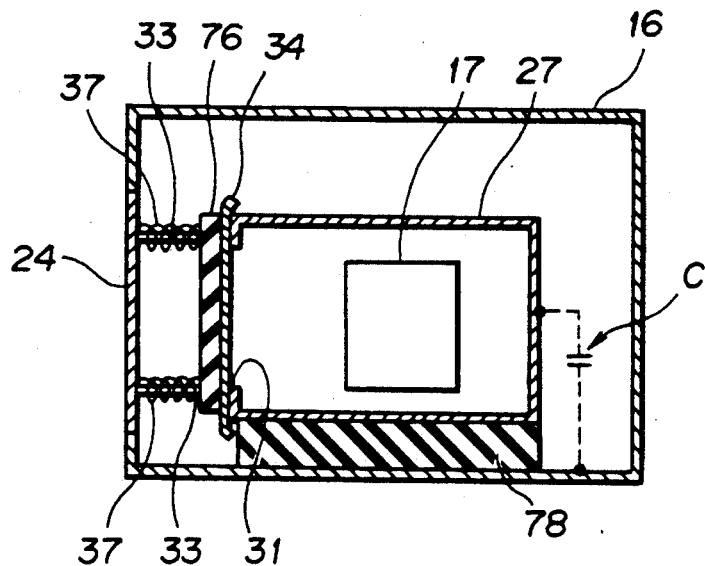
Figure 40:
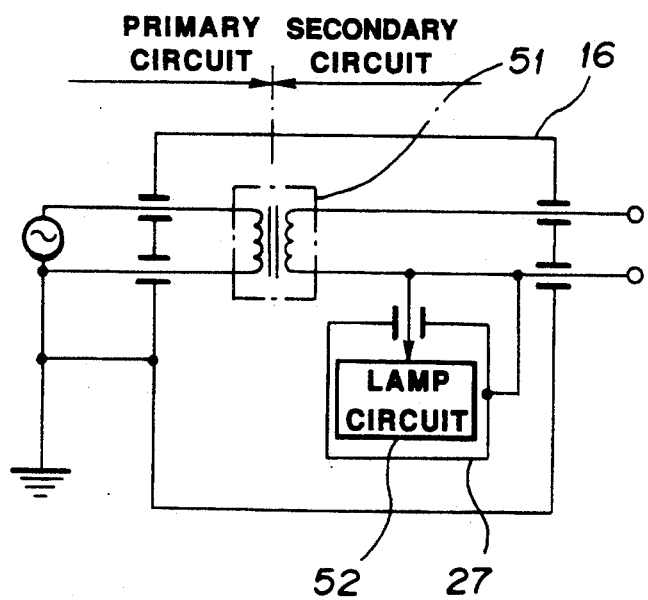

The electric state of the case 16 and inner case 27 shall be explained by using FIGS. 39 and 40.

In FIG. 39, as the fitting member 78 is provided between the inner case (shielding box) 27 and case 16, the cases 16 and 27 will be electrically insulated from each other. The net 56 of the inner door 34 closes the opening 31 and is conductive with the inner case 27 to enclose the lamp 17 which is an electromagnetic wave generating source together with the inner case 27. The net 56 is electrically insulated from the opening and closing door 24 by the holding member 76. As shown in the circuit diagram in FIG. 40, a primary circuit and secondary circuit are electrically separated from each other by a transformer 51 so that the inner case (shielding box) 27 may be insulated from the case 16, that is, the primary circuit so as to be electrically floating. Further, the case 16 is grounded. The interior of the inner case 27 is electrically connected to the secondary circuit. The inner case 27 may be separated as a single body.

In this embodiment, when the opening and closing door 24 is closed, the net 56 will close the opening 31 of the inner case 27. As the net 56 is fitted to the frame member 77, the frame member will be pressed against the inner case 27 so that the electromagnetic wave generating source lamp 17 will be enclosed with the inner case 27, net 56 and frame member 77. The net 56 will be conductive with the inner case 27. In such a state, the noise radiated from the lamp 17 will be dropped to the secondary circuit from the net 56.

In this embodiment, the same as in the above mentioned respective embodiments, as the primary circuit and secondary circuit are separated from each other, safety can be secured and the radiation of electromagnetic wave noise can be reduced.

In FIG. 39, in the circuit shown by the broken lines, the inner case 27 and the case 16 may be connected with each other in the alternating current. In this case, the noise on the secondary side can be bypassed while securing safety.

The other formations, operations and effects are the same as in the first embodiment.

Figure 41:
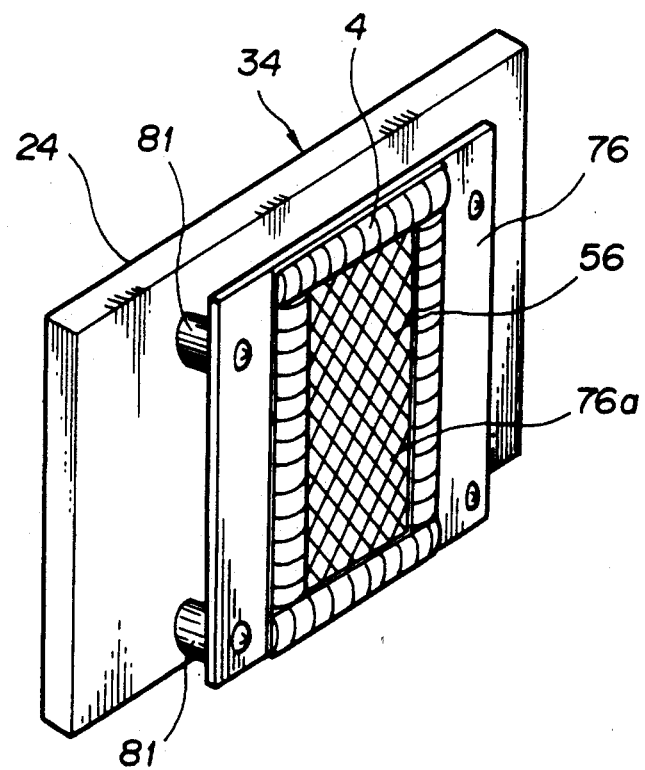
FIG. 41 relates to the ninth embodiment of the present invention and is an explanatory view of an opening and closing part.

FIG. 41 shows the ninth embodiment of the present invention.

This embodiment is the same as the eighth embodiment except that an electroconductive finger member 4 is provided in place of the pins 33, E-rings 36 and coil springs 37. The same component members as in the first and eighth embodiments shall bear the same reference numerals and shall not be explained here.

Figure 1:
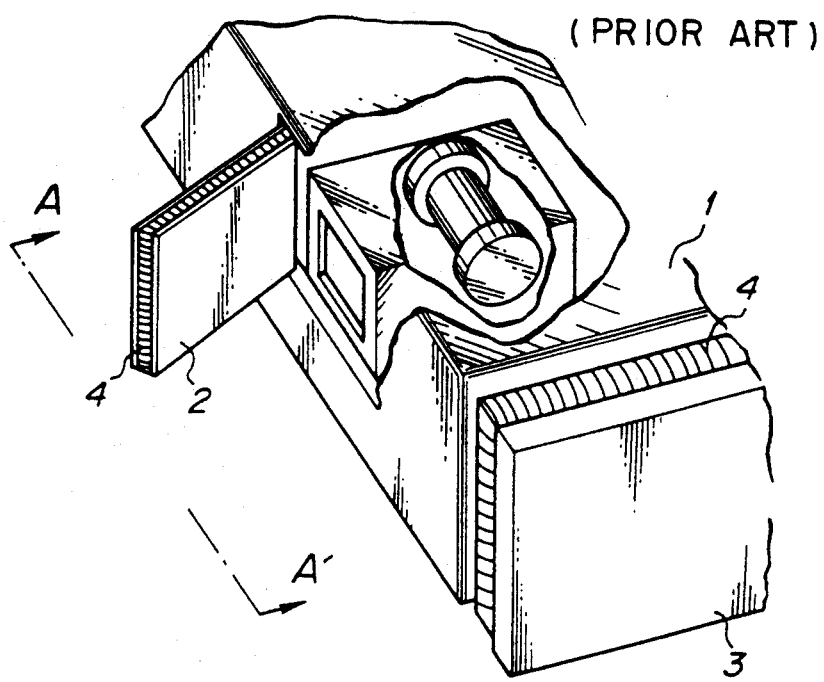
Figure 2:
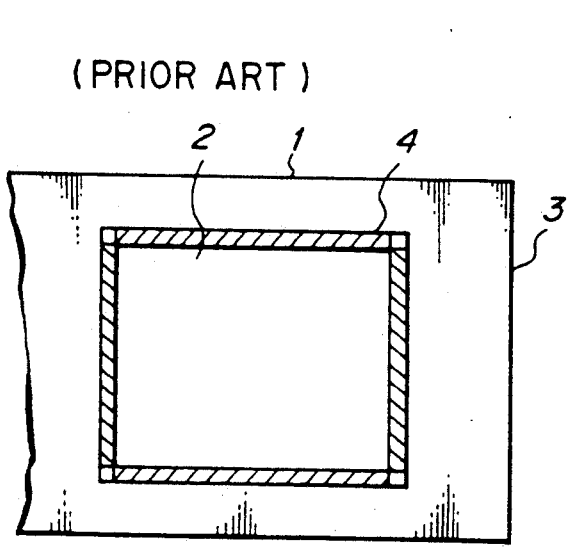
Figure 3A:
Figure 3B:
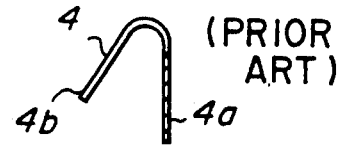

In this embodiment, the holding member 76 described in the eighth embodiment is fixed to an opening and closing door 24 with a fixed distance kept from the opening and closing door 24 by spacers 81. The electroconductive finger member 4 shown in FIG. 3 is provided on the periphery of the vent 76a of the holding member 76. Further, a net 56 is provided to be conductive to the electroconductive finger member 4 so as to close the vent 76a.

In this embodiment, when the opening and closing door 24 is closed, the electroconductive finger member 4 will be pressed against the inner case 27 so as to be transformed and will become conductive with the inner case 27. The net 56 will close the opening 31 of the inner case 27 and will reduce the radiation of the electromagnetic wave noise from the opening 31.

The inner case 27 is electrically insulated from the case 16.

The other formations, operations and effects are the same as in the first and eighth embodiments.

Figure 42:
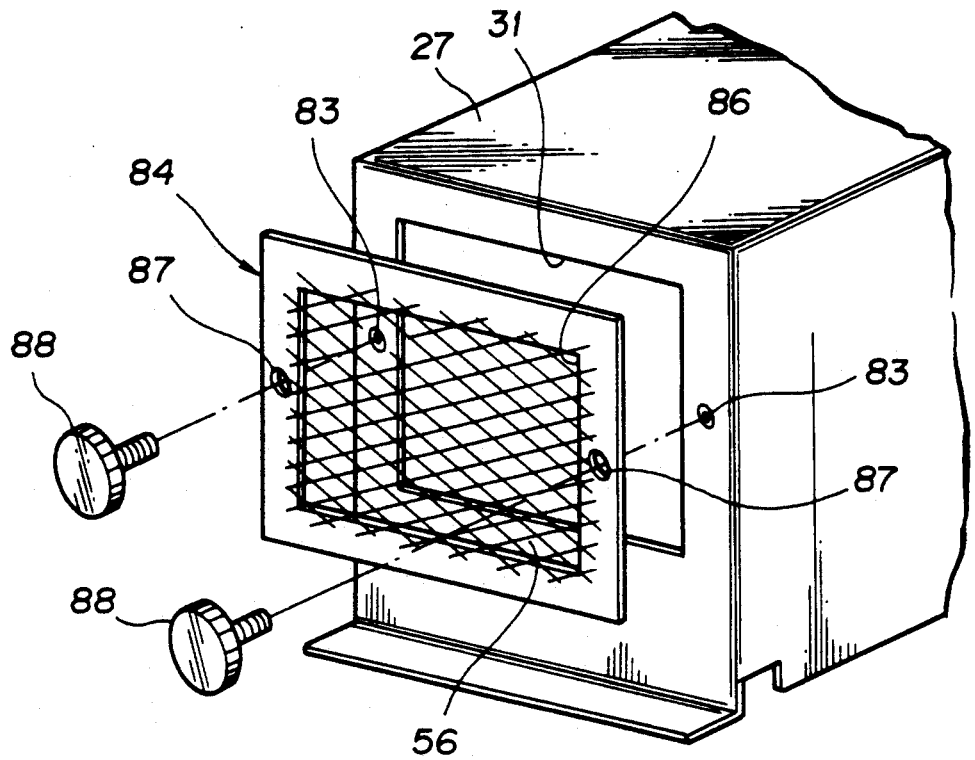
FIG. 42 relates to the tenth embodiment of the present invention and is an explanatory view of an opening of an inner case.

FIG. 42 shows the tenth embodiment of the present invention. The same component members as in the first embodiment shall bear the same reference numerals and shall not be explained here.

In this embodiment, the opening and closing door 24 and inner door 84 are not operatively connected with each other.

Within a case 16 of this embodiment, an inner case 27 is provided to be conductive with the case 16. The inner case 27 is provided with an opening 31 facing the opening and closing door 24. Screw holes 83 are provided near the opening 31. The inner case 27 is provided with an inner door 84 so as to close the opening 31. The inner door 84 is formed to be plate-like of an electroconductive material, is provided in the center with a vent 86 and is further provided with fitting holes 87 so as to coincide with the positions of the above mentioned screw holes 83. The screw parts of the fitting screws 88 are inserted respectively through the fitting holes 87 and are further screwed respectively into the screw holes 83 to fix the inner door 84 to the inner case 27. Also, the above mentioned vent 86 is fitted with a net 56 so as to close it.

In this embodiment, in case the lamp 17 which is an electromagnetic wave generating source is to be replaced, the opening and closing door 24 is opened, the fitting screws 88 are loosened and taken away and the inner door 84 is removed. Then, the lamp 17 is replaced and the inner door 84 is again fixed to the inner case 27 with the fitting screws 88 so that the opening 31 of the inner case may be closed with the net 56. When the inner door 84 is fitted, the net 56 and inner case 27 will be conductive with each other and the noise radiated from the lamp 17 will be dropped to the ground through the case 16 from the inner case 27 or the net 56.

In this embodiment, as the inner door 84 is not operatively connected with the opening and closing door 24, the formation can be made simpler than in the above mentioned respective embodiments.

The other formations, operations and effects are the same as in the first embodiment.

Figure 43:
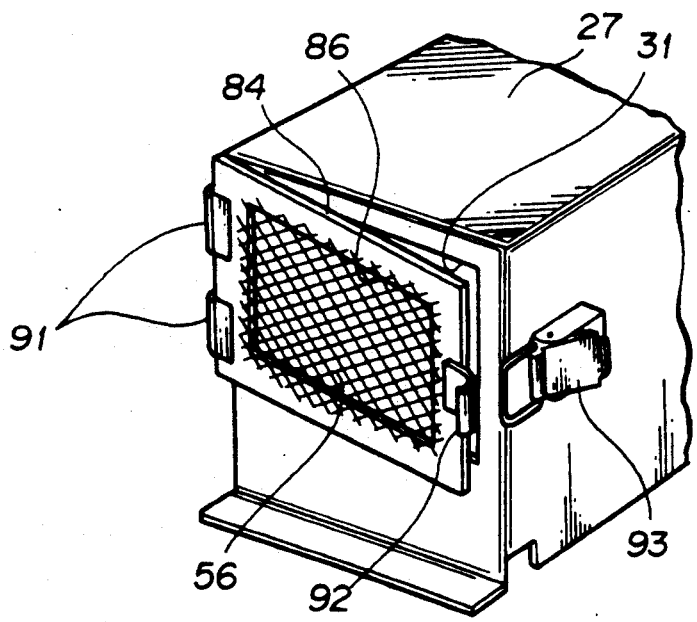
FIG. 43 relates to the 11th embodiment of the present invention and is an explanatory view of an opening of an inner case.

FIG. 43 shows the 11th embodiment of the present invention. The same component members as in the first and tenth embodiments shall bear the same reference numerals and shall not be explained here.

In this embodiment, the inner door 84 described in the tenth embodiment is fitted to the inner case 27 through hinges 91 so as to be free to open and close. A hook member 92 is fixed to the inner door 84 so as to be engaged with a locking piece 93 provided on the inner case 27 to be able to close the opening 31 with the inner door 84.

The other formations and operations are the same as in the first and tenth embodiments.

Also, this embodiment has the same effects as the first and tenth embodiments. The tenth and eleventh embodiments may be the applied also to the eighth embodiment electrically insulating the inner case 27 and inner door 84 from the case 16.

As explained above, according to the present invention, as the electromagnetic wave generating source is enclosed with the inner case and inner door which are made conductive with each other, the electromagnetic wave noise to the circuit provided within the case can be reduced and, as the inner door or the like will be hidden within the case while in use, the appearance can be made favorable.

What is claimed is:

1. An endoscope light source apparatus reducing radiation of electromagnetic wave noise comprising:
an inner case, formed of at least a material which is electrically conductive, in which a light source generating electromagnetic waves is housed, said inner case formed with a first opening for replacing said light source;
an inner door kept conductive with said inner case and closing said first opening to enclose said light source together with said inner case; and a case formed of at least a material which is electrically conductive, said case housing said inner case and having a second opening for replacing said light source and an opening and closing door for closing said second opening.

2. An endoscope light source apparatus reducing radiation of electromagnetic wave noise comprising:

an inner case formed of at least a material which is electrically conductive, said inner case housing a light source generating electromagnetic waves and said inner case formed with a first opening for replacing said light source;

an inner door kept conductive with said inner case and closing said first opening to enclose said light source together with said inner case;

a case formed of at least a material which is electrically conductive, said case housing said inner case and having a second opening for replacing said light source and an opening and closing door for closing said second opening; and a closing means for opening and closing said inner door as operatively connected with the opening and closing of said opening and closing door.

3. An endoscope light source apparatus according to claim 1 or 2 wherein said inner case is kept conductive with said case.

4. An endoscope light source apparatus according to any of claims 1 or 2 wherein said inner case is electrically insulated from said case.

5. An endoscope light source apparatus according to claim 3 wherein said opening and closing door is made conductive with said inner door.

6. An endoscope light source apparatus according to claim 2 wherein said closing means includes a bar-like member fixed to said opening and closing door to hold said inner door and an elastic member provided on said bar-like member to press said inner door against said inner case.

7. An endoscope light source apparatus according to claim 2 wherein said closing means includes an elastic member provided between said opening and closing door and said inner door.

8. An endoscope light source apparatus according to claim 7 wherein said elastic member is an electroconductive rubber.

9. An endoscope light source apparatus according to claim 7 wherein said elastic member is a plate spring.

10. An endoscope light source apparatus according to claim 2 wherein said closing means has a link mechanism formed between said opening and closing door and said inner door so that, when said opening and closing door is closed, said inner door will be closed.

11. An endoscope light source apparatus according to claim 2 wherein said closing means comprises a bar-like member fixed to said opening and closing door to hold said inner door, an elastic member provided on said bar-like member to press said inner door against said inner case and an insulating member electrically insulating said opening and closing door and said inner door from each other.

12. An endoscope light source apparatus according to claim 2 wherein said closing means comprises a holding member fixed to said opening and closing door to hold said inner door, an insulating member held by said holding member to electrically insulate said opening and closing door and said inner door from each other and a connecting member provided on said inner door to connect said inner case and said inner door with each other.

13. An endoscope light source apparatus according to claim 1 or 2 wherein said inner door is formed of an electroconductive net of a mesh size corresponding to a frequency of electromagnetic wave noise to be reduced.

14. An endoscope light source apparatus according to claim 13 wherein said inner case has an air intake port for taking in air which cools said light source and for discharging air out of said electroconductive net of said inner door.

15. An endoscope light source apparatus according to claim 14 wherein said air intake port has an electroconductive net of a mesh size corresponding to said frequency of said electromagnetic wave noise to be reduced and for closing said air intake port.

16. An endoscope light source apparatus according to claim 1 or 2 wherein said inner case has an emitting port for emitting illuminating light output from said light source closed with an electroconductive net of a mesh size corresponding to a frequency of electromagnetic wave noise to be reduced.

17. An endoscope light source apparatus according to claim 14 wherein said opening and closing door has a vent discharging air sucked in through said air intake port.

18. An endoscope light source apparatus according to claim 1 wherein said light source is arranged in a part positioned on a periphery within said case and near said opening and closing door.

19. An electric apparatus reducing radiation of electromagnetic wave noise comprising:

an inner case formed of at least a material which is electrically conductive, said inner case housing an electromagnetic wave generating source and, said inner case formed with a first opening for replacing said electromagnetic wave generating source;

an inner door closing said first opening to enclose said electromagnetic wave generating source together with said inner case; and a case formed of at least a material which is electrically conductive, said case housing said inner case and having a second opening for replacing said electromagnetic wave generating source and an opening and closing door for closing said second opening.

20. An electric apparatus according to claim 19 wherein said electromagnetic wave generating source is a light source generating an illuminating light to be fed to an endoscope.

21. An electric apparatus according to claim 19 wherein said electromagnetic wave generating source is a digital circuit.

* * * * *